(12) United States Patent
Burkett

(10) Patent No.: US 9,076,186 B2
(45) Date of Patent: Jul. 7, 2015

(54) OPT-IN COLLECTOR SYSTEM AND METHOD

(71) Applicant: Digital Health Dialog, LLC, South Lake, TX (US)

(72) Inventor: Kenneth Burkett, South Lake, TX (US)

(73) Assignee: Digital Health Dialog, LLC

( * ) Notice: Subject to any disclaimer, the term of this patent is extended or adjusted under 35 U.S.C. 154(b) by 246 days.

(21) Appl. No.: 13/644,219

(22) Filed: Oct. 3, 2012

(65) Prior Publication Data

US 2013/0218595 A1  Aug. 22, 2013

Related U.S. Application Data

(63) Continuation-in-part of application No. 12/463,446, filed on May 11, 2009, now Pat. No. 8,452,608.

(51) Int. Cl.
| | |
|---|---|
| *G06Q 50/00* | (2012.01) |
| *G06Q 50/22* | (2012.01) |
| *H04L 29/06* | (2006.01) |
| *G06Q 30/02* | (2012.01) |
| *G06F 19/00* | (2011.01) |
| *G06Q 50/24* | (2012.01) |
| *G06Q 40/00* | (2012.01) |

(52) U.S. Cl.
CPC ............. *G06Q 50/22* (2013.01); *H04L 67/42* (2013.01); *G06Q 30/0234* (2013.01); *G06F 19/3456* (2013.01); *G06Q 30/02* (2013.01); *G06Q 50/24* (2013.01); *G06F 19/328* (2013.01); *G06Q 40/00* (2013.01)

(58) Field of Classification Search
CPC ...................................................... G06Q 50/22
USPC ...................................................... 705/2, 3
See application file for complete search history.

(56) References Cited

U.S. PATENT DOCUMENTS

2011/0246218 A1* 10/2011 Starko .............................. 705/2

* cited by examiner

*Primary Examiner* — Michelle L Le
(74) *Attorney, Agent, or Firm* — The Law Firm of H. Dale Langley, Jr., P.C.

(57) ABSTRACT

Systems request and collect an opt-in from a network-connected communications device. The communications device has a unique identifier address. A server computer is connected to the network. A detector connects to a data channel over which the unique identifier address passes, and determines the unique identifier address. A dispatcher connected to and controlled by the server computer creates an opt-in request message directed to the communications device at the unique identifier address. A database is connected to the server computer. A record of the database is created for the communications device, which record includes the opt-in request message and unique identifier address. The server computer communicates the opt-in request to the communications device, and any reply message of the opt-in is received from the communications device and the database record updated accordingly. The opt-in reply message is a HIPAA authorization in a prescription drug benefit system.

35 Claims, 18 Drawing Sheets

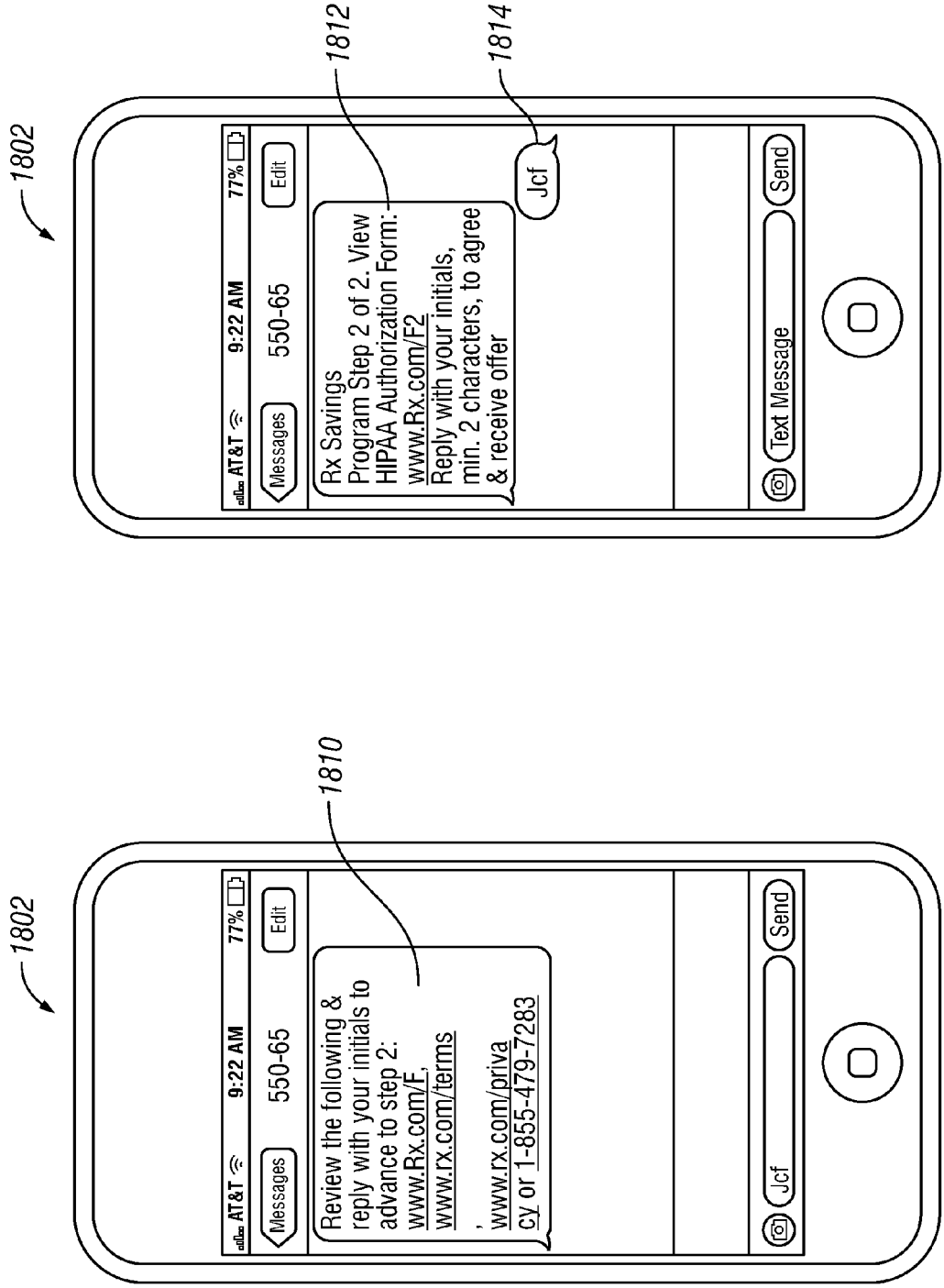

OPT-IN COLLECTOR SYSTEM AND METHOD

CROSS-REFERENCE TO RELATED APPLICATIONS

The present application is a continuation-in-part and has benefit of priority of U.S. patent application Ser. No. 12/463,446, titled "Wireless Cellular Systems and Methods for Prescription Drug Discounts and Therapy Delivery", filed May 11, 2009, which application is co-pending and has at least one same inventor of the present application and is herein incorporated by this reference.

TECHNICAL FIELD

The present invention generally relates to systems and methods for collecting opt-in permissions, and more particularly relates to systems and methods of automatedly detecting an identifier of an opt-in candidate communications device and soliciting and obtaining an opt-in of the device through communications over a computer network.

BACKGROUND

An opt-in is often a condition to participation in a program, service, transaction, sale, discount, rebate or other offering. The term "opt-in" is used herein in a broad sense to refer to any election, authorization, consent, permission, agreement or approval.

Conventionally, an opt-in is an action by a person in response to a received request to the person asking for the opt-in as a condition to something next. In order to direct the request to the person, identity of the individual or of a device operated by the individual must be known. Such personal identifying information, however, can be subject to privacy and security requirements or restrictions. For instance, various laws, regulations and standards in the U.S., as well as various other countries, may restrict or limit access or use of certain information and require secure handling and transmission of such information. Also, contractual or other strictures may impose privacy or security obligations related to certain information. It would be advantageous, however, to direct a request for opt-in to a person or device when the individual or personal information is not identifiable or is restricted or subject to secrecy requirements.

A particular example, from among others, where personal identity and information are subject to secrecy and privacy requirements or restrictions is certain health care information. For example, the U.S. Health Insurance Portability and Accountability Act of 1996, together with related privacy and security rules (HIPAA), established national standards in the U.S. for privacy and security of certain health information that is identifiable with a particular person. HIPAA generally applies to many health plans, clearinghouses and certain health care providers and related services transmitting health information in electronic form. Under HIPAA, "individually identifiable health information", which includes information relating to physical or mental health and health care of an individual that can be used to identify the individual, can be subject to privacy and security restrictions as "protected health information" (PHI). PHI can include, as examples, name, address, birth date, Social Security Number, and the like.

Other laws, rules, standards, customs or trade practices can similarly apply in other industries or jurisdictions to various information transmitted or maintained. HIPAA, as well as certain others, establishes an opt-in regime for certain use or disclosure of PHI. Under the HIPAA opt-in regime, a Covered Entity (under the law) must obtain an opt-in permission from an individual in order to use or disclose PHI of the individual for payment, treatment or healthcare operations (i.e., a "consent") and also for any marketing and other non-payment/treatment/healthcare operations use (i.e., an "authorization"). The opt-in permission may be a "consent" Similar opt-in regimes are required, or conventionally employed in any event, to obtain prior consent to use or disclosure of other personal information of individuals, such as, for example, financial information, electronic communications, wireless device location, cable subscriptions, computer security, video rentals, taxpayer information, and others.

The various opt-in laws, rules, standards, customs and practices pose a dilemma to individuals desiring access to new goods and services and options therefor, and to marketers of those various goods and services who wish to provide access to the individuals. In particular, because individually identifiable information may be restricted, that information may not be known for individuals in order to apprise them of availability of goods, services and options. Thus, the limited access to personal information of the individuals may prevent them from being made aware of goods, services and available options that would be desirable. More simply, it has not been possible to present an individual with a request for an opt-in to receive information of goods, services and available options, because of restrictions on access of the individual's personally identifiable information.

In the case of prescription drug benefits, as one non-exclusive example, a medical patient conventionally obtains a written (or an electronic or telephonic, as applicable) script for a prescription drug from a physician to address the patient's malady. The patient carries the written script to a pharmacy (or the physician communicates the electronic or telephonic script to the pharmacy, as applicable). The pharmacy fills the prescription. The patient makes payment and picks-up the prescription drug at the pharmacy. The price paid by the patient is the pharmacy's charge for the drug less any covered benefit under the patient's insurance. The pharmacy collects the covered benefit amount from the insurer. Streamline of this conventional prescription drug delivery process would benefit patients, and also pharmacies and other health providers. Moreover, patients, pharmacies and health providers would benefit if the patient is made aware of drugs and options, for example, other suitable drugs, discounts, and insurance benefits that may be available to the patient, as well as other possibilities.

In this conventional prescription drug delivery scheme, the pharmacist typically counsels the patient in proper use of the drug at point of pick-up by the patient at the pharmacy. During the patient's visit to the physician's office, the physician may also provide the patient with drug use and protocol instruction. These instructions (whether from pharmacist and/or physician) may be verbal, written, or combination. Typical instructions may include proper drug use procedures, regimen schedule, importance of regimen compliance, and others. After the patient's contact with the pharmacist and physician, the patient must retain and recollect the instructions, in whatever form received. Often, the patient's only next opportunity to confirm the instructions is a subsequent face-to-face contact with the physician or pharmacist, such as through a later physician office or pharmacy visit for a medication check-up or prescription refill.

Physicians, pharmacies, insurers, and other pharmaceutical and health providers are interested in targeting helpful and applicable information to prescription drug patients. Time and access constraints of these providers limit opportunity for disseminating such information to the patient. Benefit insurers, for example, wish to encourage patient compliance to drug therapy regimen and to promote healthy practices. Physicians desire greater access to patients for increased awareness of patient efforts and concerns during drug therapy, such as would assist improving and varying drug treatment as appropriate. Pharmacies similarly wish to assist patients by providing helpful targeted information, addressing patient questions, and promoting health and marketing initiatives.

Patients desire access to any special offers or discounts for specific prescription drugs, to uniquely targeted information to gain knowledge and assistance in medication therapy, proper drug usage and health practices, and to any available options therefor. Patient access to credible sources of information has conventionally been limited because periods of the patient's direct contact with physicians, pharmacists and other health providers are often time constrained. Patients, moreover, may not have ability to assess credibility of information that may be available from third party sources. Additionally, even where the patient has been provided credible relevant information (such as by physician, pharmacy or other reliable source), patients may misplace such information or tend to disregard the information if not readily and easily accessible. Targeted drug and health information, including discounts and other offers, uniquely relevant to the patient and applicable prescription, would be beneficial if readily accessible to patients.

Cellular telephones and other wireless devices are a prevalent mode of communication for many consumers. These consumers include prescription drug patients and patient caregivers. Cellular devices can provide features for voice calls, messaging, calendar, scheduling, Internet access, and other operations. Cellular telephones, for example, in addition to voice call capabilities, often have short message service (SMS), multimedia message service (MMS), enhanced message service (EMS), wireless access protocol service (WAP), and/or other messaging features for sending and receiving mobile text and multimedia communications.

It would, therefore, be desirable to provide new and improved systems and methods for collecting opt-ins in view of privacy and other restrictions that may apply to individually identifiable information. It would also be desirable to provide new and improved systems and methods of requesting and collecting those opt-ins in view of restricted personal information. Additionally, it would be desirable to facilitate individuals in obtaining goods and services, such as prescription drugs, using most convenient modes of communication for the individuals.

SUMMARY

An embodiment of the invention is a system for requesting and collecting an opt-in from an entity via a communications device of the entity communicatively connected to a communications network. The communications device has a unique identifier address of the communications network. The system includes a server computer communicatively connected to the communications network, a data channel for communicating the unique identifier address, a detector communicatively connected to the data channel to determine the unique identifier address communicated on the data channel, a dispatcher communicatively connected to and controlled by the server computer, an opt-in request message created by the dispatcher and directed to the communications device at the unique identifier address of the communications network, a database communicatively connected to and controlled by the server computer, and a record of the database created by the database for the communications device of the unique identifier address, the record includes items representing the opt-in request message and unique identifier address. The server computer communicates the opt-in request message to the communications device over the communications network.

Another embodiment of the invention is a method for requesting and collecting an opt-in from an entity via a communications device of the entity communicatively connected to a communications network. The communications device has a unique identifier address of the communications network. The method includes detecting the unique identifier address passing through a data channel communicating the unique identifier address, receiving the unique identifier address from the step of detecting by a server computer, creating an opt-in request message directed to the unique identifier address, communicating the opt-in request message over the communications network to the unique identifier address for receipt by the communications device, and creating a record of a database representing the opt-in request message and the unique identifier address.

Yet another embodiment of the invention is a system for requesting and collecting an opt-in from an entity via a communications device of the entity communicatively connected to a communications network. The communications device has a unique identifier address of the communications network. The system includes a server computer communicatively connected to the communications network, an enrollment form communicatively connected to the server computer, the enrollment form includes the unique identifier address, a dispatcher communicatively connected to and controlled by the server computer, an opt-in request message created by the dispatcher and directed to the communications device at the unique identifier address of the communications network, a database communicatively connected to and controlled by the server computer, and a record of the database created by the database for the communications device of the unique identifier address, the record includes items representing the opt-in request message and unique identifier address. The server computer communicates the opt-in request message to the communications device over the communications network.

Another embodiment of the invention is a method for requesting and collecting an opt-in from an entity via a communications device of the entity communicatively connected to a communications network. The communications device has a unique identifier address of the communications network. The method includes receiving an enrollment form that includes the unique identifier address, by a server computer communicatively connected to the communications network, creating an opt-in request message based on the enrollment form, directed to the unique identifier address, communicating the opt-in request message over the communications network to the unique identifier address for receipt by the communications device, and creating a record of a database representing the opt-in request message and the unique identifier address.

Another embodiment of the invention is a system for requesting and collecting an opt-in from an entity via a communications device of the entity communicatively connected to a communications network. The communications device has a unique identifier address of the communications network. The system includes a server computer communicatively connected to the communications network, an offer card including at least a call number and an offer code, the offer code and the unique identifier address received by the server computer via the call number over the communications network from the communications device, a dispatcher communicatively connected to and controlled by the server computer, an opt-in request message created by the dispatcher to correspond to the offer code, and directed to the communications device at the unique identifier address of the communications network, a database communicatively connected to and controlled by the server computer, and a record of the database created by the database for the communications device of the unique identifier address, the record includes items representing the opt-in request message and unique identifier address. The server computer communicates the opt-in request message to the communications device over the communications network.

Yet another embodiment of the invention is a method of requesting and collecting an opt-in for HIPAA authorization from an entity via a communications device of the entity communicatively connected to a communications network. The communications device has a unique identifier address of the communications network. The communications network includes a text messaging link to the communications device. The method includes receiving by a server computer communicatively connected to the communications network, the unique identifier address of the communications device, creating an opt-in request message directed to the unique identifier address, communicating the opt-in request message over the communications network by the server computer to the unique identifier address, for receipt by the communications device over the text messaging link, and creating a record of a database representing the opt-in request message and the unique identifier address.

Another embodiment of the invention is a method of delivering a prescription drug discount via a cellular message on a cellular carrier network. The method includes receiving a message artifact of a prescription token by a server computer at the destination address, the prescription token comprises at least data representing one instructor, including a prescription drug identity, a prescription drug patient identity, a cell phone number related to the prescription drug patient identity, and at least one destination locator for a server computer communicatively connected to the cellular carrier network, parsing the message artifact by the server computer, generating the prescription token by the server computer after the step of parsing, looking-up at least a portion of the prescription token in an eligibility database connected to the server computer, the eligibility database comprises at least one eligibility record related to the at least the portion of the prescription token, retrieving the at least one eligibility record from the step of looking-up at least a portion of the prescription token, looking-up at least a portion of the at least one eligibility record in a discount database, the discount database comprises at least one discount artifact related to the prescription drug identity of the at least one instructor, retrieving the at least one discount artifact of the discount database from the step of looking-up the at least a portion of the at least one eligibility record, processing the at least one discount artifact by the server computer to generate a discount coupon, sending the discount coupon by the server computer for receipt by a cellular communication device over a cellular carrier network, receiving the discount coupon, together with a drug prescription per the prescription drug identity of the at least one instructor, by a pharmacy gateway by the cellular communication device, communicating the drug prescription, together with the prescription drug patient identity of the at least one instructor, to a benefit processor by the server computer, determining a coverage benefit by the benefit processor based on the drug prescription and the prescription drug patient identity, communicating the coverage benefit to the pharmacy gateway, communicating an eligibility update notification to the server computer by the benefit processor, after the step of communicating the coverage benefit to the pharmacy gateway, receiving the eligibility update notification by the server computer, updating the at least one eligibility record of the eligibility database via the server computer, in response to the eligibility update notification, processing the eligibility update notification to derive a prescription refill date related to the at least one eligibility record, and storing the prescription refill date in the eligibility record.

In further aspects of the embodiments, the method includes, if the step of looking-up the prescription token fails because the eligibility record is not in the eligibility database, prior to the step of retrieving the eligibility record, generating an eligibility record by the eligibility database based on the prescription token.

In yet other aspects of the embodiments, the updating of the method includes processing the eligibility update notification by the benefit processor to revise the eligibility record.

In other further embodiments, the coverage benefit is selected from the group consisting of: an insured coverage and a non-insured coverage; and the method includes, if an insured coverage is the coverage benefit, determining by the pharmacy gateway a first discount per the coverage benefit and the discount coupon, for the drug prescription, and, if a non-insured coverage is the coverage benefit, determining by the pharmacy gateway a second discount per solely the discount coupon, for the drug prescription.

In additional embodiments, the eligibility database comprises a plurality of eligibility records, and each of the eligibility records includes the prescription drug identity, the drug patient identity, the prescription refill date, and the cell number relationally linked to the drug patient identity, and the method includes filtering the plurality of the eligibility records at a date in time, based on the date in time and relation to the prescription refill date of the eligibility records, retrieving a subset of the plurality for the prescription drug identity, the prescription refill date relative to the date in time, and the cell number relationally linked to the respective drug patient identity and the prescription drug identity, looking-up the prescription drug identity of the subset in the discount database to obtain a respective discount coupon for each prescription drug identity of the subset, retrieving the respective discount coupon, sending the respective discount coupon to the cell number relationally linked to the applicable drug patient identity and the drug identity of the relevant eligibility record(s), and repeating for the entire subset and all prescription drug identities of the subset.

Another embodiment of the invention is a system for delivering a prescription drug discount to a cell phone via a cellular message of a carrier network. The prescription drug discount relates to a prescription script. The system includes a server computer communicatively connected to the cell phone via the carrier network, a prescription token related to the prescription script, received by the server computer, an eligibility database and a discount database of the server computer, the server computer controls the eligibility database and the discount database in response to receiving the prescription token, a discount coupon of the discount database, communicated by the server computer to the cell phone at the phone number via the carrier network, in response to receiving the prescription token, a pharmacy gateway communicatively connected to the cell phone, to receive the discount coupon from the cell phone and the prescription script, a benefit processor communicatively connected to the pharmacy gateway and the server computer, including a database, a benefit artifact of the database relationally associated to the discount coupon and the prescription script, a first communicator connected to the benefit artifact, for communicating the benefit artifact to the pharmacy gateway, and a second communicator connected to the benefit artifact, for communicating the benefit artifact to the server computer. The server computer updates the eligibility database in response to receiving the benefit artifact from the second communicator of the benefit processor.

In other aspects of the embodiments, the system includes a follow-up coupon of the discount database, communicated by the server computer to the cell phone at the phone number via the carrier network, in response to receiving the prescription token.

In yet other aspects of the embodiments, the system includes a memory of the cell phone connected to the radio and the processor. The follow-up coupon is stored in the memory in response to receiving the follow-up coupon by the cell phone.

BRIEF DESCRIPTION OF THE DRAWINGS

The present invention is illustrated by way of example and not limitation in the accompanying figures, in which like references indicate similar elements, and in which:

FIGS. 18A-E illustrate exemplary MMS messages viewed on a beneficiary device, for example, as delivered to the beneficiary device by the system of FIG. 17, according to certain embodiments of the invention.

DETAILED DESCRIPTION

Figure 11:
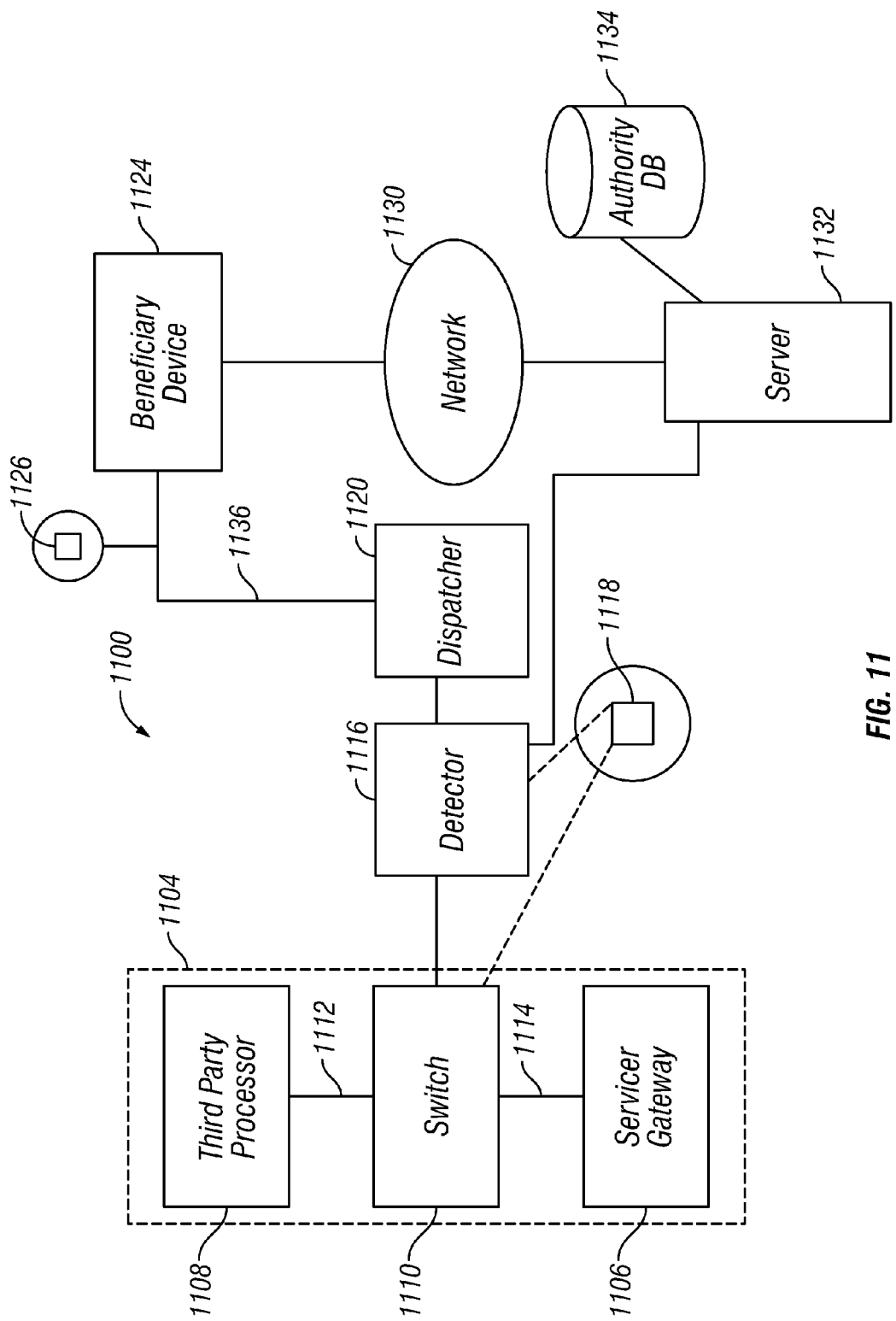
FIG. 11 illustrates a system for determining a benefit element at a switch to request and collect an opt-in from a beneficiary device, according to certain embodiments of the invention.

Referring to FIG. 11, a system 1100 for requesting and collecting opt-ins is communicatively connected to a data system 1104. The data system 1104 is, for example, devices and communications links of a three party payment system, such as present in prescription drug payment arrangements. The data system 1104 includes at least one servicer gateway 1106 and at least one third party processor 1108. A switch 1110 communicatively connects the servicer gateway 1106 to the third party processor 1108. The data system 1104 can include more than one servicer gateway 1106 and/or more than one third party processor 1108, and the switch 1110 in such instance communicatively connects respective servicer gateways 1106 with an appropriate third party processor(s) 1108 for processing benefits in relation to the particular servicer and beneficiary entitled to benefits in connection with goods or services of the servicer.

The servicer gateway 1106 communicatively connects to the switch 1110 by a communications link 1114. The servicer gateway 1106 includes one or more communications device, for example, point of sale (POS) device, a computer, or other processing device, which may include, for example, processor, memory, software program modules, input/output devices, and network connectors. The servicer gateway 1106 also may, but need not necessarily, include or communicatively connect to other processing device(s), computer(s), memory, database(s), and communications network(s) (not shown in FIG. 11), of same or other servicer entity(ies), locations, affiliates, or otherwise. The third party processor 1108 communicatively connects by a communications link 1112 to the switch 1110, and includes one or more processor, for example, a server computer, memory, and database of beneficiaries, servicers and relevant benefits. The third party processor 1108 may, but need not necessarily, also include or communicatively connect to other devices and operations, for example, computers, databases, or the like of a sponsor of a benefits plan, an administrator of a benefits plan, or others. The servicer gateway 1106, the switch 1110 and the third party processor 1108, together with any devices of these others, communicate, coordinate and exchange benefits data representing beneficiaries, servicers, third party processors, and applicable claims and benefits, in order to receive, process, adjudicate and fulfill claim requests and obligations for benefits with respect to applicable servicers, third party processors, and beneficiaries.

In the data system 1104, communications between the servicer gateway 1106 and the third party processor 1108, via the switch 1110, conform to particular format for records exchange between the servicer gateway 1106 and the third party processor 1108. For example, records of electronic claims for benefits may conform to one or more formats according to standards for electronic data interchange (EDI). In the case of prescription drug benefits, records communicated between the servicer gateway 1106 and the third party processor 1108 conform to data interchange standards of the National Council for Prescription Drug Programs (NCPDP). The NCPDP record formats include fields and data elements for various items regarding prescription transactions, including, for example, field number, field name, field type, field format, and field length positions for transaction format for prescriptions, which may include a bank identifier (BIN), a control number (PCN), and a group identifier (Group ID) in the case of prescription drug benefits.

A detector 1116 of the system 1100 is communicatively connected to the switch 1110. The detector 1116 determines at the switch 1110 any benefit element 1118 communicated by the switch 1110 between respective servicer gateway(s) 1106 and benefit processor(s) 1108. The benefit element 1118 represents one or more identifier of a benefit. For example, the benefit element 1118, in the case of a data system 1104 in a third party payment system for insurance benefits, may represent one or more identifier of a particular type of benefit or claim for the benefit, a select insurer, carrier, employer, company, or group sponsor for insurance corresponding to the benefit, or other criteria or characteristic relevant to a benefit. In the case of communications regarding a prescription drug benefit, the benefit element 1118 may be, for example, a BIN, a PCN, a Group ID, select combinations of these, or other identifiers, corresponding to a particular benefit, insurer, carrier, employer, company, group sponsor, and/or beneficiary.

A dispatcher 1120 of the system 1100 is communicatively connected to the detector 1116. The dispatcher 1120 is responsive to the detector 1116, upon the detector 1116 determining the benefit element 1118 at the switch 1110. On determining the benefit element 1118 at the switch 1110, the detector 1117 signals the dispatcher 1120 to obtain a unique device identifier, for example, a telephone number, messaging number, e-mail address, messaging address, network address, or other address or identifier, for a beneficiary device 1124 in respect of the benefit element 1118. The dispatcher 1120 formats a message 1126, via the unique device identifier and corresponding to the benefit relevant to the benefit element 1118. The dispatcher 1120 communicatively connects to the beneficiary device 1124 at the device identifier for the beneficiary device 1124, for communicating the message 1126 to the beneficiary device 1124.

The message 1126 communicated by the dispatcher 1120 to the beneficiary device 1124 includes at least an offer code for an offer relevant to the benefit element 1118 and an opt-in request corresponding to terms of the offer in respect of the offer code. In the case of prescription drug benefits, for example, the offer code is an identifier of the offer, such as a number, alphabet sequence, word, or combination, and the opt-in is agreement to terms and conditions and to waiver or consent to disclosure of personal information for purposes of HIPAA, with respect to the offer. On receiving the message 1126, the beneficiary device 1124 can, if opt-in is desired, input the offer code and opt-in via the beneficiary device 1124 and send an opt-in, in reply to the message 1126, over a data/messaging network 1130.

A server computer 1132 of the system 1100 is communicatively connected to the data/messaging network 1130 to receive the reply, if any, from the beneficiary device 1124. A database 1134 is included in or communicatively connected to the server computer 1132. The server computer 1132 controls the database 1134 in response to receiving the reply from the beneficiary device 1124, to log the reply, including the offer code, the device identifier for the beneficiary device 1124, and the opt-in from the beneficiary device 1124 in respect of the benefit element 1118 (and, consequently, the offer).

The server computer 1132 is communicatively connected to the detector 1116, for example, by the data/messaging network 1130 or another communications link(s). The detector 1116 communicates to the server computer 1132 the benefit element 1118, or, alternately, data representing, identifying or relating to the benefit element 1118, upon detecting the benefit element 1118 at the switch 1110 by the detector 1116. In certain non-exclusive examples, the detector 1116 communicates to the server computer 1132 at least an offer code and device identifier for the beneficiary device 1124 of or corresponding to the benefit element 1118. In response, the server computer 1132 controls the database 1134 to perform a look-up of the benefit element 1118 or relevant data representing the benefit element 1118. If the database 1134 then has logged any prior reply of the particular beneficiary device 1124 for the same benefit element 1118, the server computer 1132 can control the detector 1116 to not signal the dispatcher 1120 to send the message 1126 to the beneficiary device 1124 and/or the dispatcher 1120 to not send the message 1126. Where the prior reply of the beneficiary device 1124 exists in the database 1134, that reply is the opt-in of the beneficiary device 1124 and further request for the opt-in need not be made. If, however, the database 1134 has not then logged any prior opt-in reply of the particular beneficiary device 1124, the detector 1116 signals the dispatcher 1120 and the dispatcher 1120 send the message 1126 to the beneficiary device 1124.

Upon receiving the reply from the beneficiary device 1124, and log of the reply in the database 1134, representing the opt-in from the beneficiary device 1124 (and, consequently, serving as the opt-in by the beneficiary), the server computer 1132 can then, because of the opt-in of the beneficiary device 1124, communicate directly over the data/messaging network 1130 with the beneficiary device 1124. For example, the server computer 1132 can communicate offer(s), targeted information messages, and otherwise, to the beneficiary device 1124 over the data/messaging network 1130.

In the system 1100, the detector 1116 is a network tap, such as a packet analyzer, probe, or filter, including (or connecting to) circuits, processor, memory, computer programs stored in memory, or combinations, for filtering, intercepting, or selecting packets or select data contents of communications passing through the switch 1110. The detector 1116 decodes, shows values of fields, and analyzes content for presence of the benefit element 1118. The detector 1116 is communicatively connected to the server computer 1132 and database 1134 and, upon detection of the benefit element 1118, communicates to the server computer 1132 the benefit element 1118 or data representing the benefit element 1118 for look-up in the database 1134. In alternatives, the detector 1116 may connect to other than the switch 1110, for example, the detector 1116 may be communicatively connected the third party processor 1108 or the servicer gateway 1106, as applicable, for detecting any presence of the benefit element 1118 in communications of these with the switch 1110.

The dispatcher 1120 of the system 1100 is an electronic messaging device capable of formatting and sending the message 1126 (i.e., the request for opt-in message) to the beneficiary device 1124 via a communication link 1136 connected to the beneficiary device. In certain examples, the dispatcher 1120 includes at least a processor, memory and a messaging software program stored in memory. The dispatcher 1120 includes or connects to an adapter for communicating the message 1126 to the beneficiary device 1124 over the communication link 1136.

The communication link 1136 is any wired or wireless telecommunications communication link or network, or combination of such links and/or networks, for example, a packet-switched data network (e.g., Internet, intranet, local area network (LAN), wide area network (WAN) or virtual private network (VPN)), a circuit switched network (e.g., public switched telephone network (PSTN)), a cellular telephone network, or a wireless data network (e.g., cellular data, WiFi, WLAN, GPS, infrared, satellite, radio frequency, or other). The dispatcher 1120 can have more than one adapter for respective different communications links or networks, for example, the dispatcher 1120 can communicate the message 1126 to the beneficiary device 1124 over one or more select link, channel or network selected by the beneficiary device 1124 and indicated from the benefit element 1118. In certain examples, the dispatcher 1120 wirelessly communicates the request to the beneficiary device 1124, if the beneficiary device 1124 is a data-enabled cellular telephone, wireless data device, or cellular interactive voice response (IVR). According to certain non-exclusive examples, the message 1126 is a text message sent by telephone number call to a messaging enabled wireless telephone, tablet, pad or other device.

The server computer 1132 of the system 1100 includes at least a processor, memory and adapter for communicating over the data/messaging network 1130 with the beneficiary device 1124. In certain alternatives, the server computer 1132 can, but need not necessarily, include the detector 1116, the dispatcher 1120, or portions or combinations.

The database 1134 of the system 1100 is included in (whole or part) or communicatively connected to the server computer 1132. The database 1134 includes records of at least any prior opt-in received from the beneficiary device 1124 in connection with the benefit element 1118 and any prior message 1126 to the beneficiary device 1124 requesting an opt-in reply in connection with the benefit element 1118. An example of the database 1134 is a relational database software program stored in memory and processed by the processor of the server computer 1132 or another processor. However, the database 1134 can be any hardware device, software module stored in memory, or combination, storing beneficiary data relevant to the benefit element 1118; for example, the database 1134 can be included in or externally accessible (such as via the third party processor 1108) to the server computer 1132, or otherwise.

The data/messaging network 1130 is any telecommunication and/or data network or combination of such networks, whether public, private or combinations of these, including, for example, a local area network, wide area network, intranet, the Internet, public switched telephone network (PSTN), wireless (e.g., cellular, WiFi, WLAN, GPS, infrared, satellite, radio frequency, or other) network, satellite network, or other wired or wireless communication link or channel or combination of links or channels. In certain examples, the data/messaging network 1130 can be the same or different, in whole or part, from links communicatively connecting the detector 1116 to the server computer, the server computer 1132 to the data system 1104, and/or the dispatcher 1120 to the beneficiary device 1124.

Figure 12:
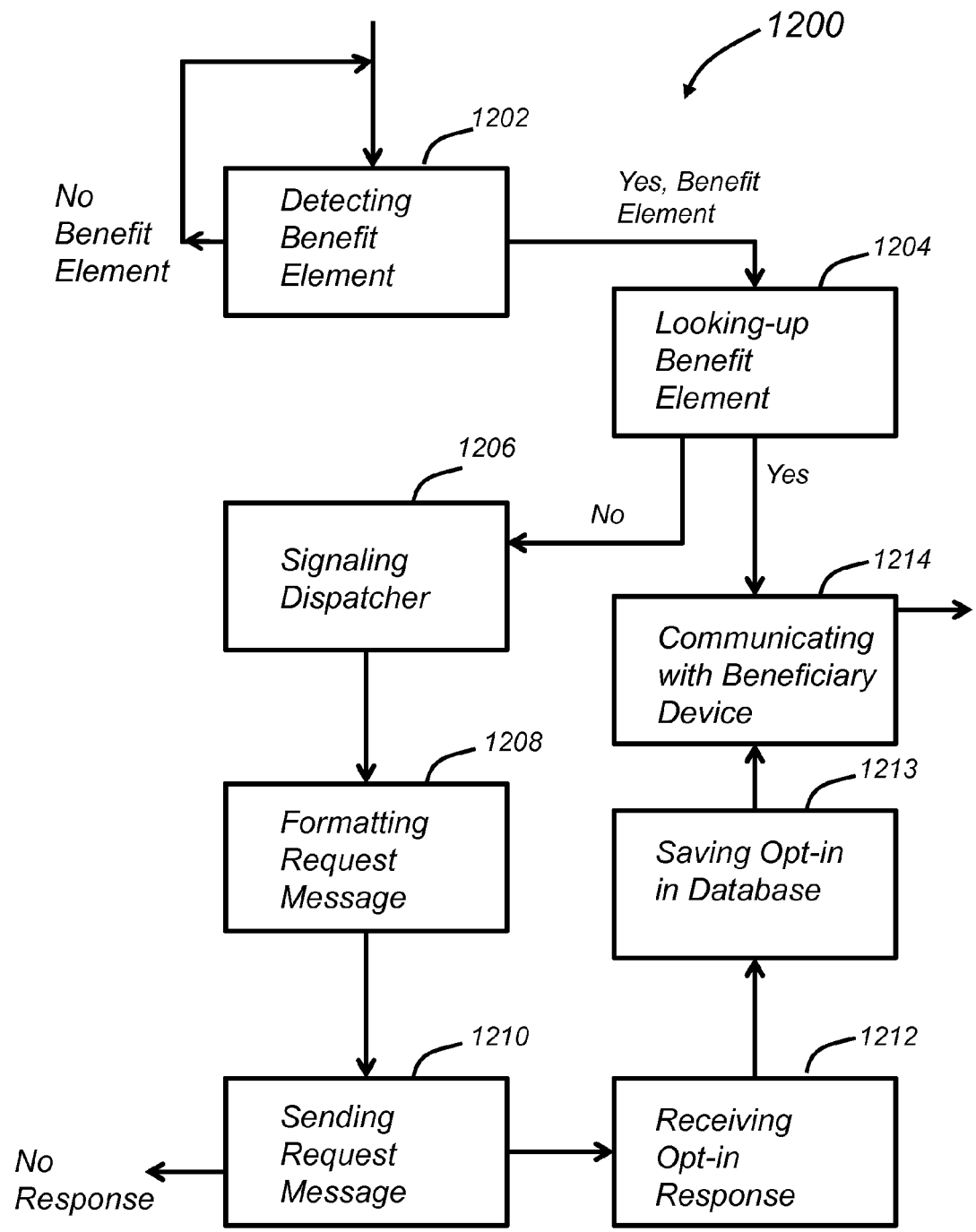
FIG. 12 illustrates a method for requesting and collecting an opt-in from a beneficiary device, according to certain embodiments of the invention.

Referring to FIG. 12, a method 1200 of requesting and collecting opt-ins, such as, for example, as may be performed by the system 1100, commences with a step 1202 of detecting a benefit element passing through a switch communicatively connecting a servicer device and a third party processor. The servicer device and the third party processor are each a communications device including or connected to a processor and memory. If no benefit element is detected in communications passing the switch, the step 1202 continues for subsequent communications.

If the benefit element is detected in the step of 1202, the benefit element detected, or data representing that benefit element, is searched 1204 in a database of received opt-ins. If an opt-in corresponding to the benefit element is not then found in the search 1204, a step of signaling 1206 notifies a dispatcher (or messenger) of the benefit element (or representative data). In a step 1208, the dispatcher formats a request message for the opt-in. The dispatcher sends the request message to an intended recipient device, for example, a beneficiary device, in a step 1210. The request message includes a request for an opt-in from the intended recipient device, and may include additional elements, such as terms of an offer, discount, participation, or other items. An example of the request is a text message to a cellular telephone as the recipient device, asking the recipient to respond via the recipient device to provide consent to terms, for example, a HIPAA consent response as the opt-in in the case of prescription drug benefits. If no response is received from the intended recipient device, the sending step 1210 ends. In certain alternatives, the sending step 1210 may be repeated more than one time, such as at selected intervals or otherwise, until there is response from the intended recipient device or the number of repeats is concluded.

If the intended recipient device responds to the sending step 1210 with the opt-in, the opt-in is received in the step 1212. The opt-in for the recipient device and the benefit element is saved in the database in the step 1213. The method 1200 continues with a step 1214 of communicating with the recipient device, such as to provide offers, discount coupons, information and the like. If on the searching step 1204 the opt-in for the recipient device and the benefit element is then already stored in the database, the steps 1206, 1208, 1210, 1212 and 1213 are bypassed and the method 1200 proceeds to the step 1214 for the recipient device and the benefit element.

Figure 13:
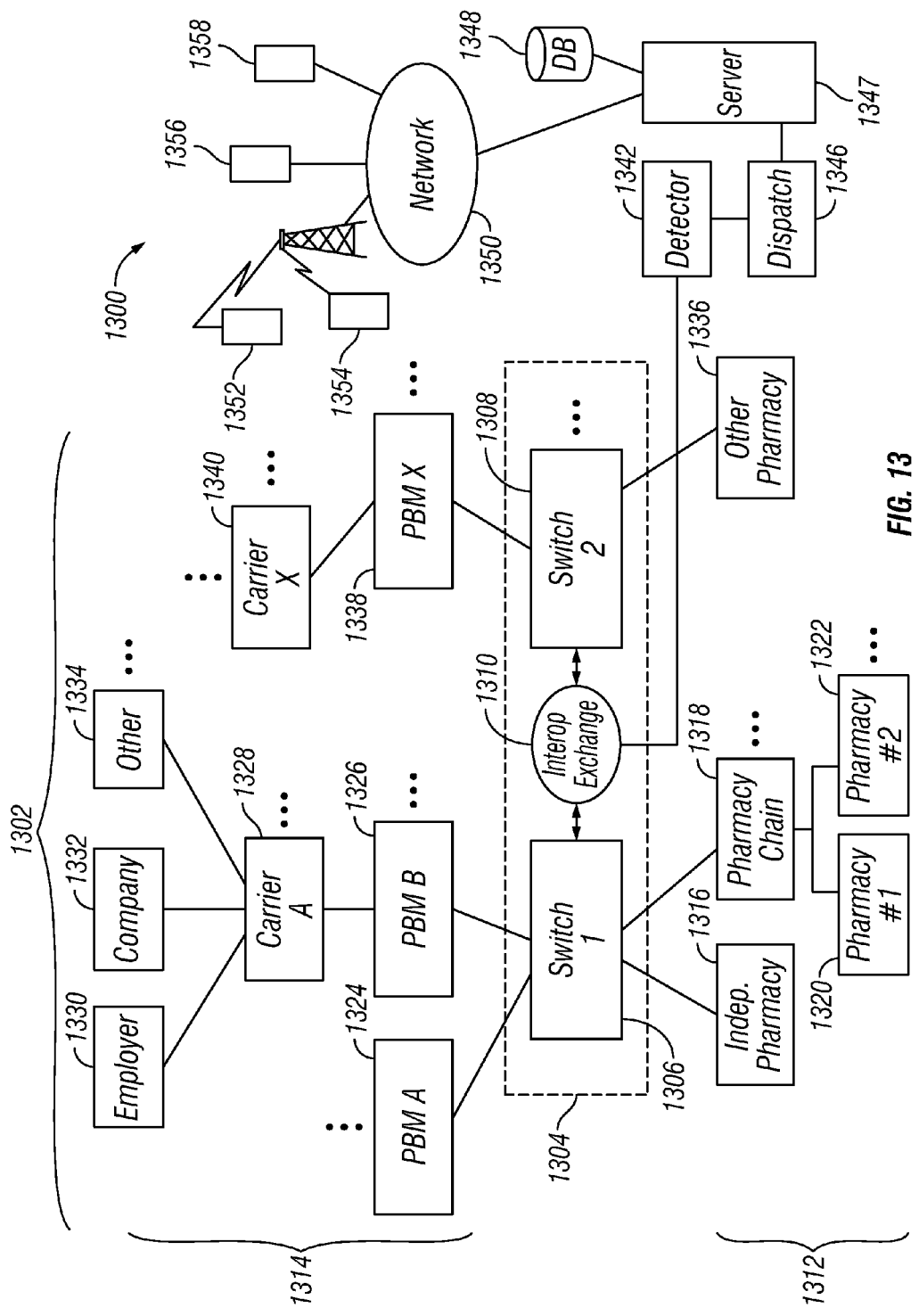
FIG. 13 illustrates a method in a prescription drug benefits system for determining an identifier of a beneficiary device and requesting and collecting an opt-in from the beneficiary device, according to certain embodiments of the invention.

Referring to FIG. 13, a system 1300 for requesting and collecting an opt-in, for example, a HIPAA opt-in of a beneficiary via a communications device of the beneficiary, is communicatively connected to a payment system 1302, such as that of a three party payment system for insurance or benefits. The payment system 1302 is intended as exemplary and may include other communicatively connected devices and units. In a three party payment system, a customer (or beneficiary) obtains a product or service from a servicer or provider and a third party payor pays all or a portion of the price. An example of such a payment system is a covered claim under insurance, in which an insurer may pay on behalf of an insured all or a portion of an amount charged by a repairer or other provider of a casualty or medical issue suffered by the insured. An example in which third party payment systems predominate is prescription drug benefits, where a pharmacy may receive payment for a prescription drug obtained by a patient from an insurer/benefit provider/government for the patient. Of course, many other examples of third party payment systems are found, including, for example, credit or debit card, PayPal™, various financial transactions, and others.

There are at least three parties in a three party payment system. As used herein in reference to a three party payment system, the term "beneficiary" is used to refer to any entity that obtains a product or service for which a third party pays or is responsible for all or a portion of the price or other consideration; the terms "servicer" and "service provider" are used interchangeably to refer to any entity that provides a product or service to a beneficiary, in return for payment or other consideration received in whole or part from a third party; and the terms "third party" and "benefit provider" are used interchangeably to refer to any entity that pays or is obligated to pay a benefit or claim to a servicer on behalf of a beneficiary provided a product or service by the servicer. The terms "benefit" and "claim" are used interchangeably herein to mean money or other consideration paid or payable by a third party to a servicer on behalf of a beneficiary under a benefits plan for the payment, such as a public or private benefits plan or program, for example, an insurance policy plan, government payment program, or other obligation or arrangement. A particular, but not exclusive, example of a benefit or claim is the money or other consideration paid or payable by a pharmaceutical drug benefit provider (e.g., private health insurer, Medicare, Medicaid, related pharmacy benefits managers (PBMs), etc.) to a pharmacy service provider (e.g., pharmacy, wholesaler, manufacturer, etc.) on behalf of a patient beneficiary obtaining a prescription drug from the pharmacy service provider.

Continuing to refer to FIG. 13, the payment system 1302 includes a switch 1304, which may, itself, include, for example, other switches 1306 and 1308 and exchange device(s) 1310 communicatively connecting the switches 1306, 1308. The switch 1304, via the switches 1306 and 1308, respectively, communicatively connects to respective servicer/provider devices 1312 and respective insurer/payer devices 1314. In the example of the payment system 1302, the switch 1306 communicatively connects to an independent pharmacy device 1316 and a pharmacy chain device 1318. The pharmacy chain device 1318 communicatively connects to pharmacy devices 1320 and 1322, for purposes of example. The switch 1306 also communicatively connects to pharmacy benefit manager (PBM) devices 1324 and 1326, and in the example, the PBM device 1326 communicatively connects to an insurer device 1328. The insurer device 1328 communicatively connects, for example purposes, to an employer device 1330, a company device 1332, and some other device 1334. Similarly, the switch 1308 communicatively connects to another pharmacy device 1336, and to a separate PBM device 1338. The PBM device 1338 communicatively connects to another insurance carrier 1340, and so on.

Although merely an example, the payment system 1302 illustrates that the switch 1304 (and its respective switches 1306, 1308, connected by exchange device 1310) connects to respective servicer/provider devices (e.g., independent pharmacy device 1316, pharmacy chain device 1318 which connects to pharmacy devices 1320, 1322, and pharmacy device 1336) and to insurer/payer devices 1314 (e.g., PBMs 1324, 1326, 1338, which connect to insurer devices 1328, 1340, and through to employer device 13330, company device 1332 and other device 1334). The switches 1304, 1306, and 1308, respectively, route communications between the appropriate servicer/provider devices 1312 (e.g., pharmacy devices 1316, 1318 and 1336, respectively), and appropriate insurer/payer devices 1314 (e.g., PBM devices 1324, 1326 and 1338, respectively). The exchange device 1310 routes communications that pass one switch 1308 to the other switch 1306, and vice versa, as appropriate, for delivering third party payments.

By way of example, but not limitation, with respect to prescription drug benefits, if a beneficiary, employed by the employer for the employer device 1330, presents a prescription for fill at the pharmacy of the other pharmacy device 1336, communications in the payment system 1302 proceed from entry to the system 1302 via input to the other pharmacy device 1336. The other pharmacy device 1336 communicates relevant data representing the prescription (such as at least a bank identifier (BIN), a control number (PCN), and a group identifier (Group ID)), and also any other requisites of NCPDP record formats for prescription drug transactions, to the switch 1308. Because the insurer/payer devices 1314 connected to the switch 1306, rather than the switch 1308, apply for the employer and beneficiary, the exchange device 1310 communicates the relevant data representing the prescription to the switch 1306. The switch 1306 communicates the data to the relevant PBM 1326 for the employer and beneficiary, and the PBM 1326 can further communicate the data to the insurer device 1328 and employer device 1330, as applicable. The reverse of this communication occurs for data representing any insured benefit or other coverage that is directed to the pharmacy at the other pharmacy device 1336 for filling and payment in connection with the prescription. One or more electronic data interchange (EDI) communication network connect the various devices of the payment system 1302 and secure protection of protected health information (PHI).

A benefit element detector 1342 of the system 1300 communicatively connects to the switch 1304 of the payment system 1302. For example, the detector 1342 connects to the exchange device 1310 or, alternately, to the switch 1306 or 1308, or both. In other alternatives, the detector 1342 connects to communication link(s) connecting the switches 1306, 1308 and exchange device 1310, to an insurer/payer device 1314, or other device or communication link of the payment system 1302 for sending or receiving data representing the prescription. The benefit element detector 1342 includes or is operatively controlled by a processor or circuit and a memory, to filter, sniff, analyze or otherwise determine if any benefit element is presented in communications passing where connected. The benefit element is, for example, a particular BIN, PCN, Group ID, or combination, of such entries, as well as a unique device identifier for a communications device of the beneficiary relevant to the benefit element, in the NCPDP record format communicated in the payment system 1302.

The benefit element detector 1342 is communicatively connected to a request dispatcher 1346 of the system 1300. The benefit element detector 1342, on determining presence of the benefit element, communicates to the dispatcher 1346 the benefit element, or data representing the benefit element, as well as the unique device identifier. The dispatcher 1346 is an electronic messaging device capable of formatting and sending an opt-in request message. The dispatcher 1346 includes or communicatively connects to at least a processor, memory and a messenger controlled by the processor, such as a messaging software program stored in memory.

A server computer 1347 of the system 1300, including at least a processor and memory, is connected to the dispatcher 1346 for receiving the opt-in request message from the dispatcher 1346, together with the unique device identifier for the relevant beneficiary device and benefit element. The server computer 1347 is communicatively connected to one or more data communications link or network 1350.

The communications network 1350 is, or can be or include, any telecommunications and/or data link or network, or combinations of such links and/or networks, public, private or combinations of these. The communications network 1350 is or can include any telecommunications and/or data link or network, or combinations of such links and/or networks, public, private or combinations of these, for example, a local area network, wide area network, intranet, the Internet, public switched telephone network (PSTN), wireless (e.g., cellular, WiFi, WLAN, GPS, infrared, satellite, radio frequency, or other) network, satellite network, or other wired or wireless communication link or channel or combination of links or channels.

An opt-in database 1348 of the system 1300 is included in or communicatively connected to the server computer 1347. The opt-in database 1348 is included in (whole or part) or communicatively connected to the server computer 1347. An example of the database 1348 is a relational database software program stored in memory and processed by the processor of the server computer 1347 or another processor. The database 1348, however, can be any hardware device, software module stored in memory, or combination. The database 1348 includes records of any prior opt-in, such as a HIPAA opt-in, received from a beneficiary via communications of a communications device (i.e., beneficiary device) of the beneficiary with the server computer 1347.

The server computer 1347 communicatively connects to various beneficiary devices, for example, a messaging enabled cellular telephone 1352 or other communications device 1354, a network-connected computer 1356 or tablet device 1358, or other network-connected communications device operated by a beneficiary. The server computer 1347 must receive an opt-in message from the beneficiary device before further communicating (via the server computer 1347 and/or other computers and devices communicatively connected to the server computer 1347) with the beneficiary device, such as to provide offers, discounts, information and the like as later described to the beneficiary via the beneficiary device.

In operation of the system 1300, the benefit element detector 1342, in communicative connection with the switch 1204, such as to the exchange device 1310, determines any benefit element in communications passing through the switch 1204, such as through the exchange device 1310. If the benefit element is detected, the detector 1342 communicates to the dispatcher 1346 the benefit element, or a data set representing the benefit element, and the unique device identifier for the beneficiary device of the beneficiary relevant to the benefit element. The unique identifier is, for example, a cellular telephone number, an IP address, or another address or contact number of the beneficiary device at which the beneficiary device is capable of receiving a request for opt-in, such as a HIPAA opt-in request, from the server computer 1347 over the network 1350.

The dispatcher 1346 receives the benefit element, or data set, and the unique device identifier from the detector 1342, and formats an opt-in request message for delivery to the beneficiary device. The opt-in request message includes terms for acceptance by reply message of the beneficiary device to the request message, and is directed to the beneficiary device for delivery over the network 1350 per the unique device identifier of the beneficiary device. The dispatcher 1346 communicates the opt-in request message to the server computer 1347 for delivery over the network 1350.

On receiving the opt-in request message, the server computer 1347 controls the database 1348 to look-up the unique device identifier and the benefit element (or an item thereof) in the database 1348. If an opt-in record corresponding to the unique device identifier and the benefit element is then stored in the database 1348, the server computer 1347 does not send the opt-in request message over the network 1350. If no opt-in record then exists in the database 1348 for the unique device identifier and the benefit element, the server computer 1347 sends the opt-in request message over the network 1350, in particular, via a certain medium or mode (e.g., wired, wireless, etc.) receivable by the beneficiary device of the unique device identifier. The server computer 1347 controls the database 1348 to create and store a record corresponding to the benefit element and the unique device identifier, and indicating that the opt-in request message is sent but no reply received.

If the beneficiary device receives the opt-in request message from the network 1350, the beneficiary device may accept and "opt-in" (e.g., provide acceptance/consent, such as for purposes of HIPAA) by sending an opt-in reply in response to the opt-in request message. The opt-in reply, via the beneficiary device, is the applicable beneficiary's contractual and legal opt-in for purposes of beneficiary consent or agreement. The opt-in reply is sent by the beneficiary device over the network 1350 to the server computer 1347.

On receiving the opt-in reply for the beneficiary device (and, consequently, the beneficiary) from the network 1350, the server computer 1347 controls the database 1348 to record the receipt of the opt-in corresponding to unique device identifier and benefit element for the beneficiary and beneficiary device.

In certain alternatives, the unique device identifier or aspects of the benefit element may be considered protected information, such as PHI, or may be accessible to a payer, insurer, PBM, servicer/provider or other third party, such as from one or more of the servicer/provider devices 1312 or an insurer/payer devices 1314. In such case, it may be necessary to obtain consent or authority of one of these parties, such as a carrier or payer, to deliver the opt-in request to beneficiaries via beneficiary devices. These parties may also authorize detection of the benefit element for particular criteria, such as where the benefit element includes particular BIN, PCN, Group ID, or other item. It is contemplated that, once an opt-in reply is received from a beneficiary device (and, consequently, the beneficiary related to the device) various services, including offers for goods or services, discounts, information, advertising and/or other items, will be communicated to the beneficiary device by the server computer 1347 (or other computers and devices communicatively connected to the server computer) as later described. Therefore, prior arrangements may be required to obtain consent or authority, as necessary, of those other parties, in order for those parties to include or make available to applicable beneficiaries the opt-in and other services (e.g., carrier or payer may include the described services as a component of insurance package offered and provided to the beneficiary). In certain instances, as well, unique device identifiers of each relevant beneficiary device may not be contained in communications detected at the switch 1304 by the detector 1342. In these instances, the dispatcher 1346 must obtain the relevant unique device identifier corresponding to each benefit element and beneficiary device in order to format and allow sending of the opt-in request to the beneficiary device. Therefore, the dispatcher 1346 and/or server computer 1347 may communicatively connect to the authorizing party (e.g., carrier, payer, etc.) to obtain the unique device identifier.

In various alternatives of the foregoing, the opt-in request sent to the beneficiary device by the server computer 1347 may address more than one opt-in(s), conditions, terms, and/or policies for acceptance or consent of the beneficiary via response to the opt-in request by the beneficiary device to the server computer 1347. For example, the opt-in request may include a request for a response comprising a HIPAA opt-in and also a consent/opt-in to terms, conditions or policies of another service or further communications of the server computer 1347. Other services and further communications may, for example, deliver offers for goods or services, discounts, information, advertising and/or other items to the beneficiary device delivering the opt-in reply.

In the embodiments, the beneficiary device can be any one or more communications device, and all types of the communications devices capable of receiving opt-in request and responding with opt-in reply over any medium or mode of communication of the network 1350 are included. In certain alternatives, the opt-in request and the opt-in reply may be communicated over different medium or mode of communication of the network 1350, for example, the opt-in request may be delivered by wireless channel and the opt-in reply delivered by wired channel. Further in alternatives, the opt-in request may be sent by more than one mode or medium of communication of the network 1350, if the beneficiary device is capable of receiving via more than one mode or medium, or if a relevant beneficiary has more than one beneficiary device with respective ones capable of communicating over different mode or medium. In other alternatives, the server computer 1347 may resend the opt-in request if no reply is received, and resending may be over same or different medium or mode of communication of the network 1350 over which the beneficiary device can communicate. Additionally in alternatives, some or all elements of the detector 1342, the dispatcher 1346, the database 1348 and the server computer 1347 may be included in or formed of others of these, for example, the dispatcher 1346 may include a messaging program stored in memory and controlled by the processor of the server computer 1347, the database 1348 may include a database program stored in memory and controlled by the processor of the server computer 1347, and otherwise.

Figure 14:
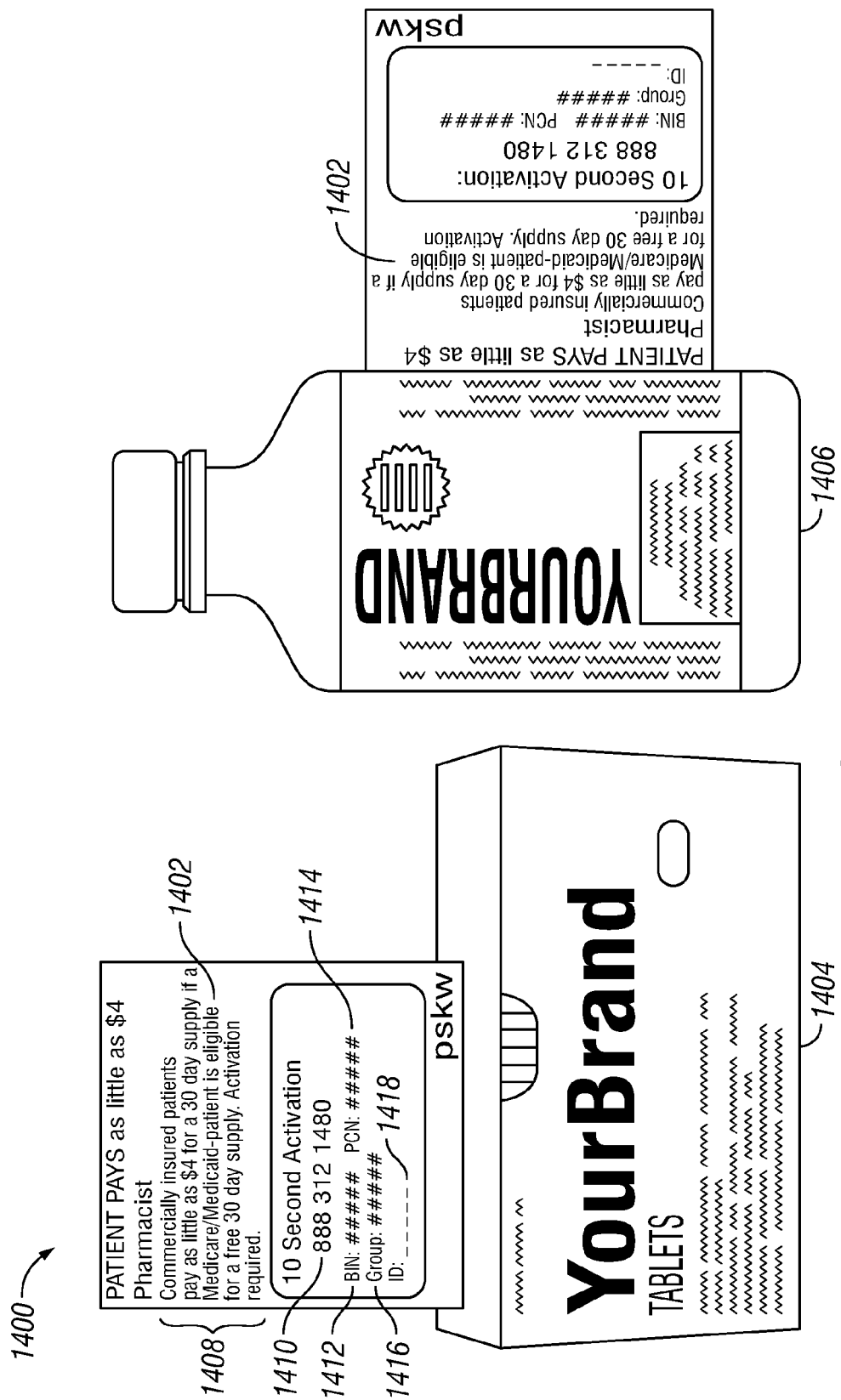
FIG. 14 illustrates a system for presenting an offer to a beneficiary to request and collect an opt-in from a communications device of the beneficiary, according to certain embodiments of the invention.

Referring to FIG. 14, another system 1400 for requesting and collecting opt-ins includes an offer code card 1402. The offer code card 1402 is affixed to or incorporated with a package, such as a box 1404, a bottle 1406 or other container. The offer code card 1402 includes an offer item 1408, and a messaging number 1410 for reply, such as a text message number for a recipient device. The card 1402 also includes a BIN 1412, a PCN 1414, a Group ID 1416, and an offer code 1418 (code not shown in detail in FIG. 14). A pharmacy, manufacturer or distributor or another in the prescription drug distribution chain, fixes the offer code card 1402 to the box 1404, the bottle 1406 or other container. On distribution of the box 1404, bottle 1406 or other container by a pharmacy to fill a prescription, the offer code card 1402 is provided with the container and filled prescription. The beneficiary of the filled prescription (or a caregiver) provided the card 1402 can then follow instructions of the offer item 1408 of the offer code card 1402, by telephone call or sending a message, such as a text message from a beneficiary's messaging device, to the messaging number 1410 and providing the offer code 1418 and any other relevant information required, such as the BIN 1412, the PCN 1414, and the Group ID 1416.

Now referring to FIG. 14, in conjunction with FIGS. 11-13, upon delivering the offer code 1418 and other relevant information, the beneficiary can then receive and send further messages as provided above. For example, the beneficiary, via one or more of the beneficiary communications device 1352, 1354, 1356, or 1358, receives an opt-in request, such as a HIPAA consent and terms and conditions of an offer, from the server computer 1347. The server computer 1347 receives from the beneficiary device any responsive opt-in reply, and thereafter the server computer 1347 makes available to the beneficiary device coupon, discount, information, and other materials and services, including as later described.

In alternatives, the offer code card may be a unitary card or note, rather than a fixture to the box 1404, bottle 1406 or container. An example of the card is a wallet- or purse-sized plastic card similar to an insurance card, credit card or the like. In other alternatives, the offer code card may be included in an insurance card or other card or note.

Figure 15:
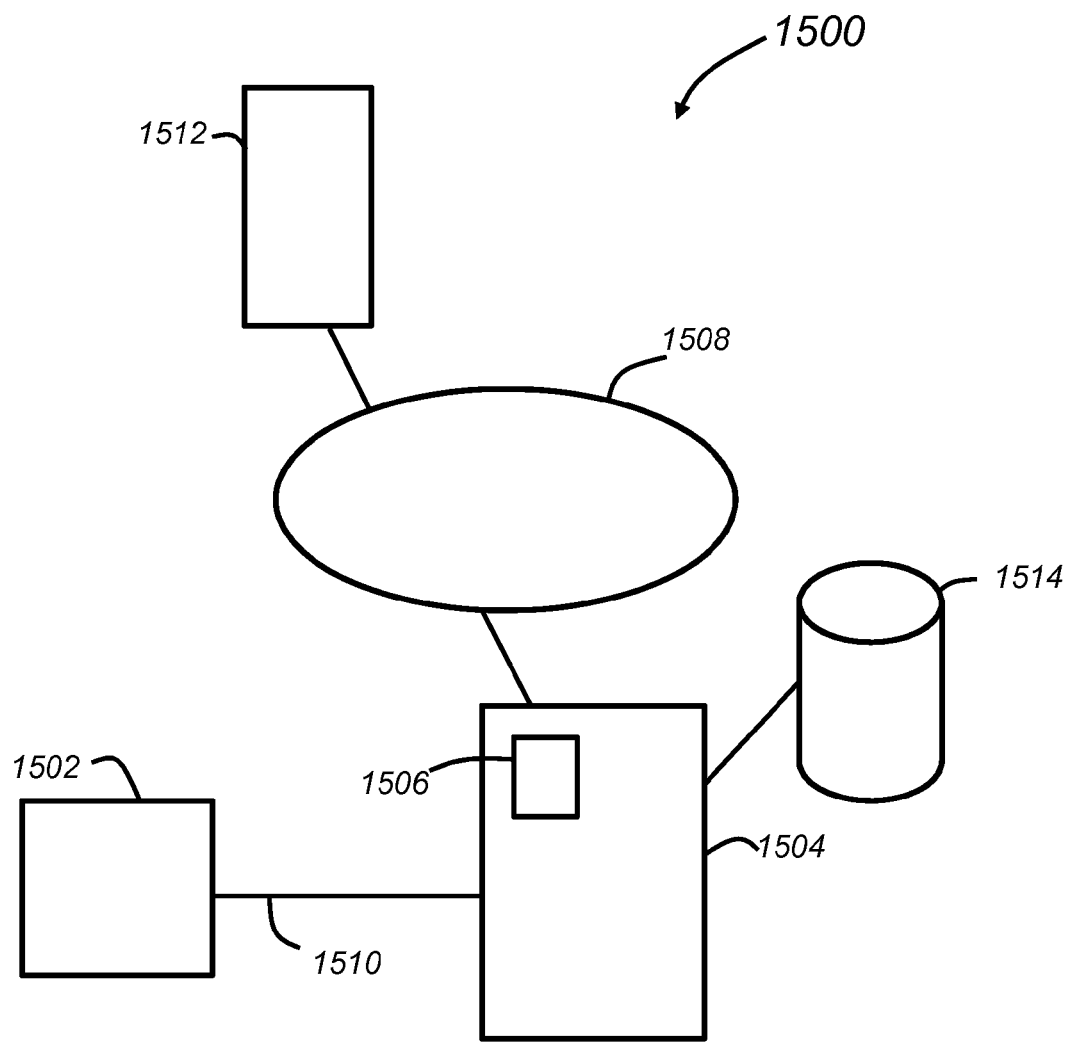
FIG. 15 illustrates a system for requesting and collecting an opt-in from a beneficiary device based on an enrollment form, according to certain embodiments of the invention.

Referring to FIG. 15, in conjunction with FIGS. 11-13, another system 1500 for requesting and collecting opt-ins includes an enrollment form 1502. The enrollment form 1502 is, for example, an XML page or other page or template, served to or accessed by a communications device (not shown in FIG. 15) of a physician's or other provider's office. As examples, the communications device can be a desktop or laptop computer, a tablet device, or other processing device capable of viewing the page or template and allowing input to provide entries. The communications device is communicatively connected to a server computer 1504, for example, by a communications link or network 1510. The communications link or network 1510 is, or can be or include, any telecommunications and/or data link or network, or combinations of such links and/or networks, public, private or combinations of these, for example, a local area network, wide area network, intranet, the Internet, public switched telephone network (PSTN), wireless (e.g., cellular, WiFi, WLAN, GPS, infrared, satellite, radio frequency, or other) network, satellite network, or other wired or wireless communication link or channel or combination of links or channels.

The server computer 1504 includes at least a processor and memory, and includes or communicatively connects to a dispatcher 1506. The server computer 1504 connects to one or more communication link or network 1508 capable of communicating with beneficiary devices, one of which is beneficiary device 1512 but may include other types of communications devices. The network 1508 is, or can be or include, any of the foregoing of network 1510, in whole or part, as well as others of the example. The dispatcher 1506 is or includes circuits, a program stored in memory, or combinations, controlled by the processor of the server computer 1504 to send and receive messages over the network 1508.

A database 1514 is communicatively connected to (or included in or stored in memory of) the server computer 1504. The database 1514 includes any records of beneficiaries and beneficiary devices, together with any corresponding opt-in, if any, previously logged in the database 1514 for the respective beneficiary device. The records include at least any prior opt-in received from the beneficiary device 1512 in connection with the parsed results of the enrollment form 1502 and any prior message(s) to the beneficiary device 1124 requesting an opt-in reply in connection with those parsed results. An example of the database 1514 is a relational database software program stored in memory and processed by the processor of the server computer 1504 or another processor.

The beneficiary device 1512 is capable of connecting to the network 1508 to receive messages from and send other messages or reply to the server computer 1504 over the network 1508. The beneficiary device 1512 includes at least a processor and memory, as well as messaging circuits, messaging program stored in memory, or combinations. Examples of the beneficiary device include, but are not limited to, a personal or laptop computer, tablet device, messaging enabled cellular phone, or other messaging device.

In operation, the physician or provider completes the enrollment form 1502 by input to the communications device, such as computer, of the physician or provider. The enrollment form 1502 is then communicated over the network 1510 to the server computer 1504. The server computer 1504 parses the enrollment form 1502 and controls the database 1514 to look up parsed results for any match then saved in the database 1514. If no match is then present in the database 1514, or if an opt-in reply has not previously been received by the server computer 1504 from the beneficiary device 1512 (or relevant beneficiary), the server computer 1504 controls the dispatcher 1506 to format and send over the network 1508 an offer request message to the beneficiary device 1512. The server computer 1504 also controls the database 1514 to create a record corresponding to the parsed results of the enrollment form 1502; however, the record indicates that an opt-in has not then been received for the particular beneficiary device 1512. If a match is then present in the database 1514, the server computer 1504 may control the dispatcher to not send an opt-in request message if the record indicates prior receipt of an opt-in reply from the beneficiary device or beneficiary. In the case of a match and record of the opt-in reply, the server computer 1504 may control the dispatcher otherwise operate; for example, send another opt-in request message or send an offer, discount or information, etc., according to rules set for the operations.

Figure 16:
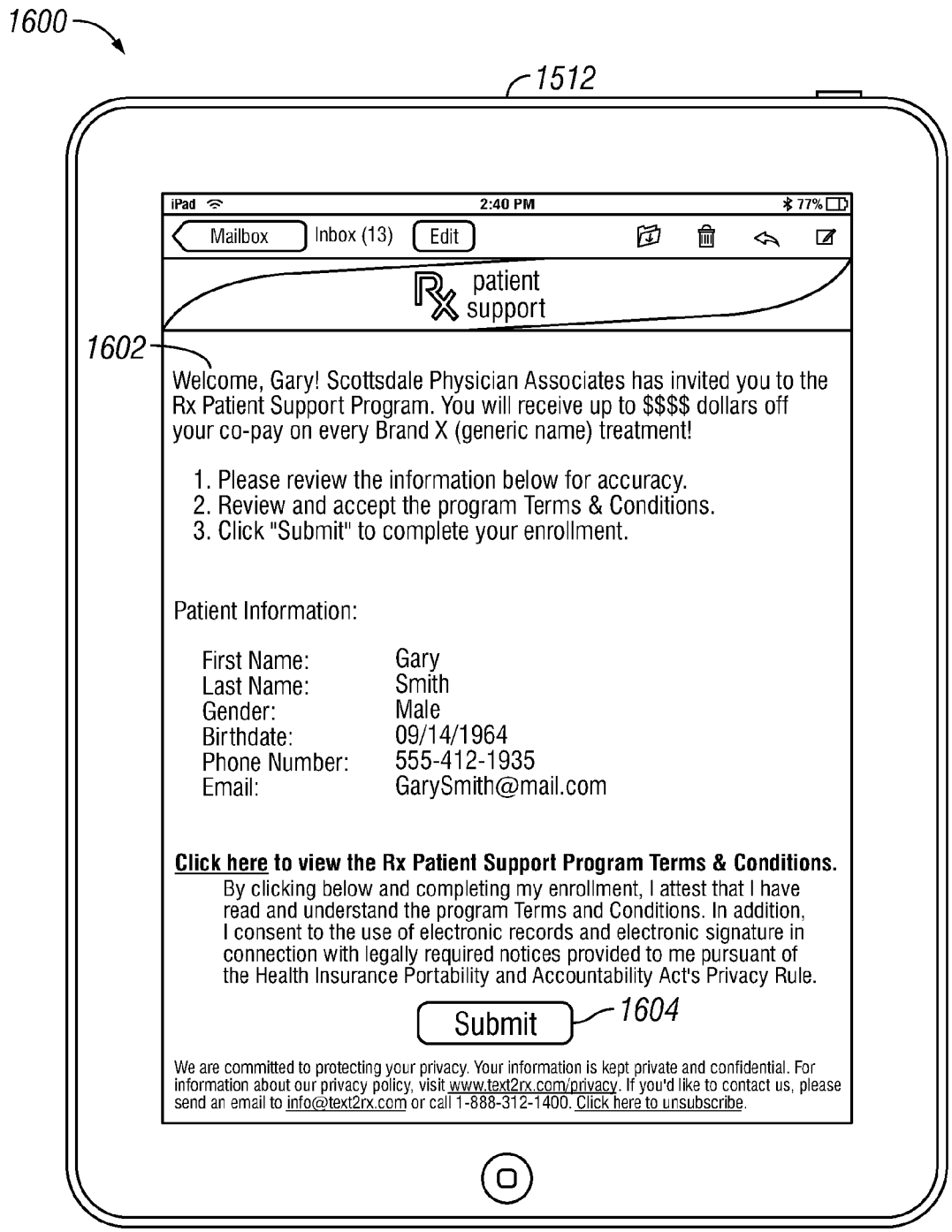
FIG. 16 illustrates an exemplary offer request message viewed on a beneficiary device, for example, in connection with the system of FIG. 15, according to certain embodiments of the invention.

Referring to FIG. 16, in conjunction with FIG. 15, an example offer request message 1600 is received and viewed by the beneficiary device 1512. The beneficiary device 1512, for purposes of example, is a tablet computer. The display 1602 of the message 1600 describes an offer available by acceptance/consent to terms, which may include HIPAA consent. Through input to a submit button 1604 of the display 1602, the beneficiary device 1512 sends an opt-in reply to the server computer 1504 over the network 1508. The opt-in reply is the opt-in of the beneficiary to terms and conditions and HIPAA consent as specified in the display 1602 and, when received by the server computer 1504, is saved in the database 1514 in the record for the beneficiary device 1512.

Figure 17:
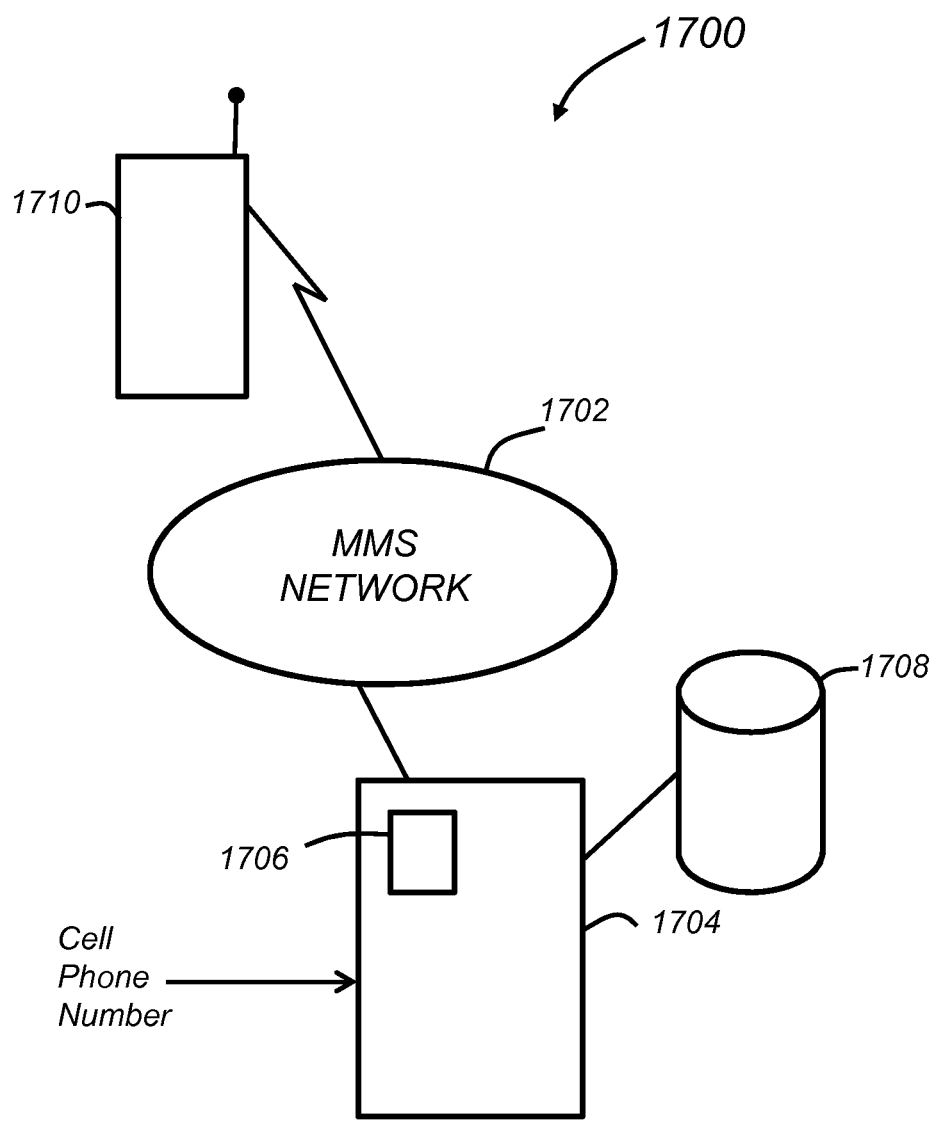
FIG. 17 illustrates a system for requesting and collecting an opt-in from a beneficiary device by MMS messaging, according to certain embodiments of the invention.

Referring to FIG. 17, a system 1700 for requesting and collecting an opt-in includes a multimedia messaging service (MMS) network 1702. The MMS network 1702 is, or can be or include, any cellular data link or network, or combinations of such links and/or networks, public, private or combinations of these, alone or in combination with any other telecommunications links or networks. The MMS network 1702 allows multimedia messages, for example, video, audio or picture messages, to be sent to messaging-enabled cell phones and other devices.

The system 1700 includes a server computer 1704, including at least a processor and memory, communicatively connected to the MMS network 1702. The server computer 1704 includes or is communicatively connected to a dispatcher 1706. The dispatcher 1706 is an MMS messaging unit, either circuits, program stored in memory and processed by a processor, or combinations, and may, but need not necessarily, be included in whole or part in the server computer 1704 or program stored in memory of and processed by the server computer 1704. A opt-in database 1708 is included in or communicatively connected to the server computer 1704. The opt-in database 1708 is, for example, a relational database stored in memory and processed by the processor of the server computer 1504 or another memory or processor. The opt-in database 1708 includes any records of relevant messaging-enabled cell phones and other devices, together with any corresponding opt-in, if any, previously logged in the database 1708 for respective cell phones and devices.

The server computer 1704 receives, from an external source, the cellular telephone or messaging call number of messaging-enabled cell phones or devices in order to send an opt-in request. The external source of the telephone or messaging call number is, for example, the cell phone or device through communication with the server computer 1704 or by a beneficiary operating the cell phone or device through direct communication to the server computer operator. Additional examples of the external source are presented by the example embodiments, such as the detector 1116, 1342 of FIG. 11 or 13 may detect the call number in communications of the benefit element passing through the switch 1104, 1304 or other devices of the Figures, the call number may be revealed or otherwise provided by the phone or device when calling to provide the offer code 1418 or other relevant items of the offer code card 1402 of FIG. 14, the call number may be provided from the enrollment form 1502 delivered to the server computer 1704 by a physician or provider communication device, or otherwise. In any event, once a call number for a cell phone or device of a beneficiary is presented to the server computer 1704, the server computer 1704 can then direct MMS messages to the cell phone or device over the MMS network 1702.

At least one beneficiary cellular device 1710, for example, a messaging-enabled cellular telephone, tablet device, personal digital assistant, or other, is communicatively connected to the MMS network 1702. The server computer 1704, on obtaining the call number of the cellular device 1710, together with relevant information for the beneficiary, such as BIN, PCN, and Group ID in respect to a prescription drug (for example, per the call in response to offer code card, the benefit element, the enrollment form or otherwise) controls the dispatcher 1706 to format an MMS message to the cellular device 1710 at the call number. The MMS message from the dispatcher 1706 is sent over the MMS network 1702 to the cellular device 1710. The server computer 1704 also controls the database 1708 to create and store a record for the cellular device 1710 and corresponding relevant information (e.g., BIN, PCN, Group ID, and offer code number) if no such record then exists in the database 1708. An MMS message, such as an opt-in request message, may then be sent to the cellular device 1710 by the server computer 1704. If a record then exists, but an opt-in has not been received, the MMS message requesting the opt-in may also be sent if in accordance with rules set for server computer 1704.

Referring to FIGS. 18A-E, in conjunction with FIG. 17, a messaging device 1802, for example, the cellular device 1710, communicates an opt-in message as follows. For purposes of example, the messaging device 1802 initiates messaging communications, to provide call number and relevant information (e.g., BIN, PCN, Group ID and offer code), to the server computer, such as in the case of the offer code card. If the server computer instead initiates messaging communications to the messaging device 1802, the initial message sent by the server computer to the messaging device 1802 may include text of similar items to that contained in the offer code card or otherwise.

Figure 18A:
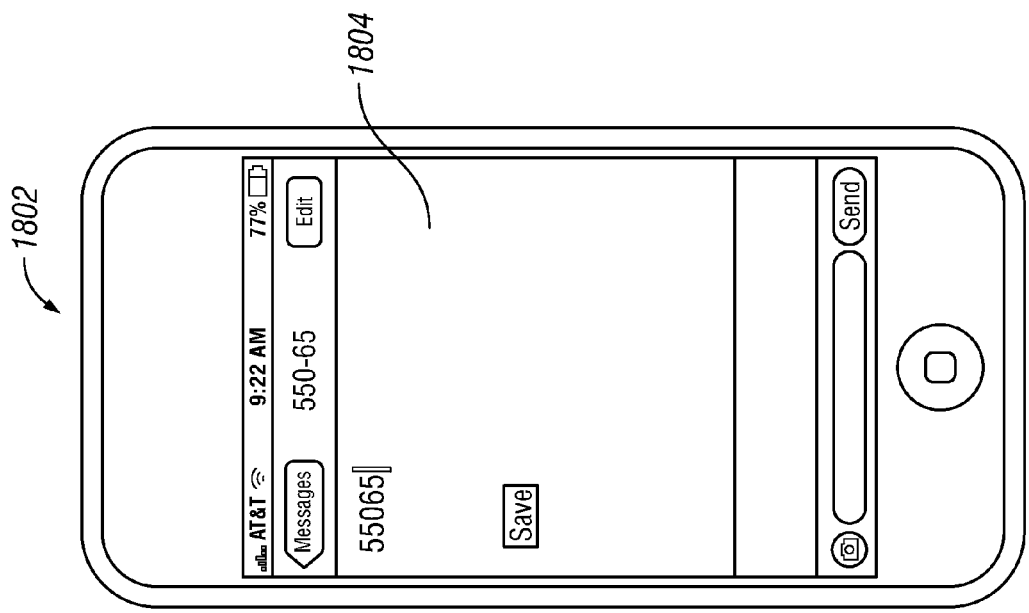
Figure 18B:
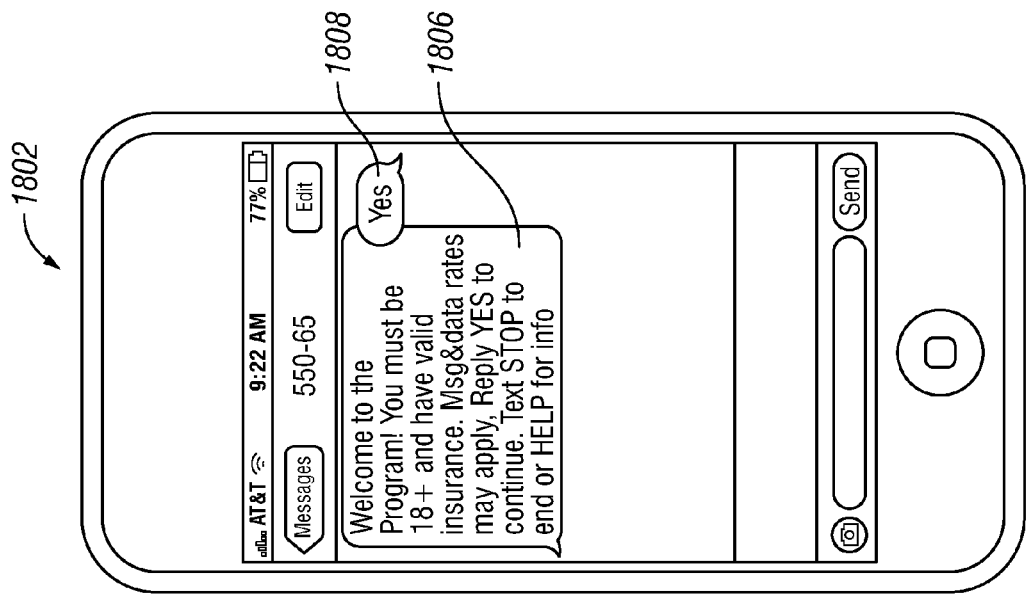

The messaging device 1802, in FIG. 18A, initially inputs the offer code and any other required text (e.g., "Save") in a text box 1804 of a messaging program stored in memory of the messaging device 1802. The messaging device 1802 inputs the call number for the server computer to receive the offer code and any text. And the messaging device 1802 sends the code message.

On receiving the code message, the server computer, via the dispatcher, formats and sends a first MMS message to the messaging device 1802. The messaging device 1802 receives and views the first MMS message 1806 as in FIG. 18B. The first MMS message 1806 includes an interactive "yes" button 1808. The messaging device 1802 may either click the "yes" button 1808 to reply to confirm age, or otherwise enter "stop" to halt the opt-in operation or enter "help" to receive more information by subsequent MMS message(s) from the server computer.

If the "yes" button 1808 is clicked, the messaging device 1802 sends an age confirmation text message to the server computer. The age confirmation text message is logged by the database in relation to the record for the messaging device 1802.

In response to the age confirmation text message, the server computer then sends a second MMS message to the messaging device 1802. The second MMS message 1810 is received and viewed by the messaging device 1802 as in FIG. 18C. The second MMS message 1810 refers to Internet website page or pages for review, and requires a message in reply containing initials of the operator of the messaging device 1802.

If initials of the operator are input to the messaging device 1802 and sent by text message to the server computer, the server computer receives the text message of the initials and the initials message is logged by the database in relation to the record for the messaging device 1802.

The server computer then sends a third MMS message to the messaging device 1802. The messaging device 1802 receives and views the third MMS message 1812 as in FIG. 18D. The third MMS message 1812 refers to Internet website page or pages for review containing a HIPAA authorization, and requires an opt-in reply message as the opt-in of the messaging device 1802 (and, consequently, the beneficiary/operator of the messaging device 1802). The third MMS message 1812 includes an interactive initials button 1814 (e.g., "Jcf" in the example). The messaging device 1802 may click the initials button 1808 to reply to the server computer with an opt-in message accepting the HIPAA authorization.

The server computer receives the opt-in message reply of HIPAA authorization from the messaging device 1802. The opt-in message reply is logged by the database in relation to the record for the messaging device 1802.

Figure 18E:
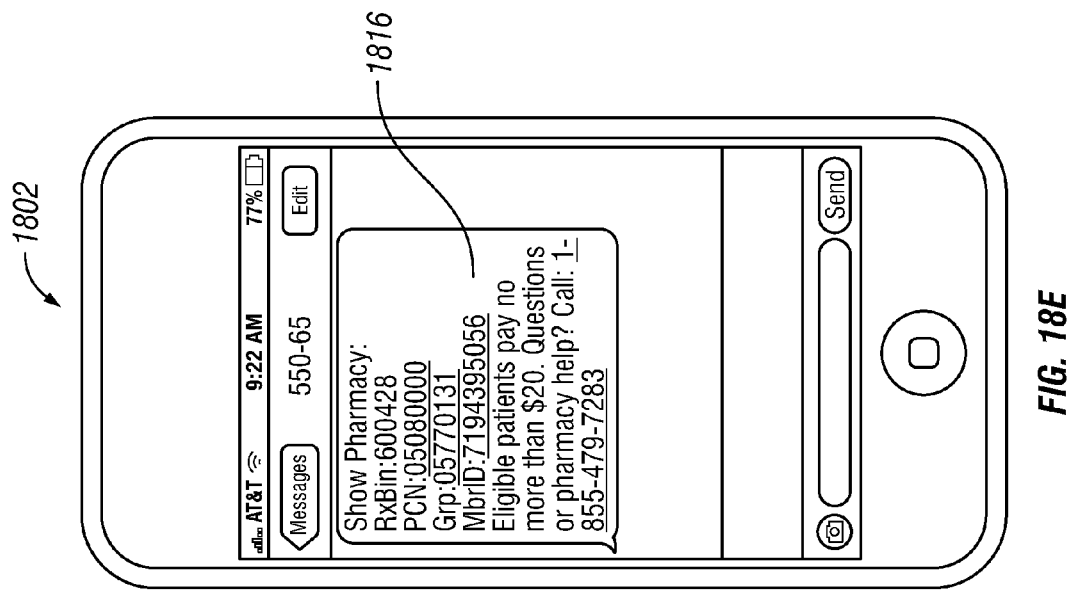

The server computer has therefore received replies of the messaging device 1802 (and the relevant beneficiary) as an opt-in to terms and conditions and to HIPAA authorization. Offer, discount, coupon, and information messages can then be sent by the server computer to the messaging device 1802, because the opt-ins are received and logged in the database. FIG. 18E is an example offer message 1816 received and viewed by the messaging device 1802. The messaging device 1802 may be presented to an applicable pharmacy for the offer of the offer message 1816, and the beneficiary is provided the discount or other award stated in the offer in connection with purchases, such as purchases of the relevant prescription drug.

The foregoing describes certain embodiments for requesting and collecting opt-ins from beneficiaries, as well as other aspects. In the following, certain embodiments for communicating to provide discounts and information are disclosed.

Figure 1:
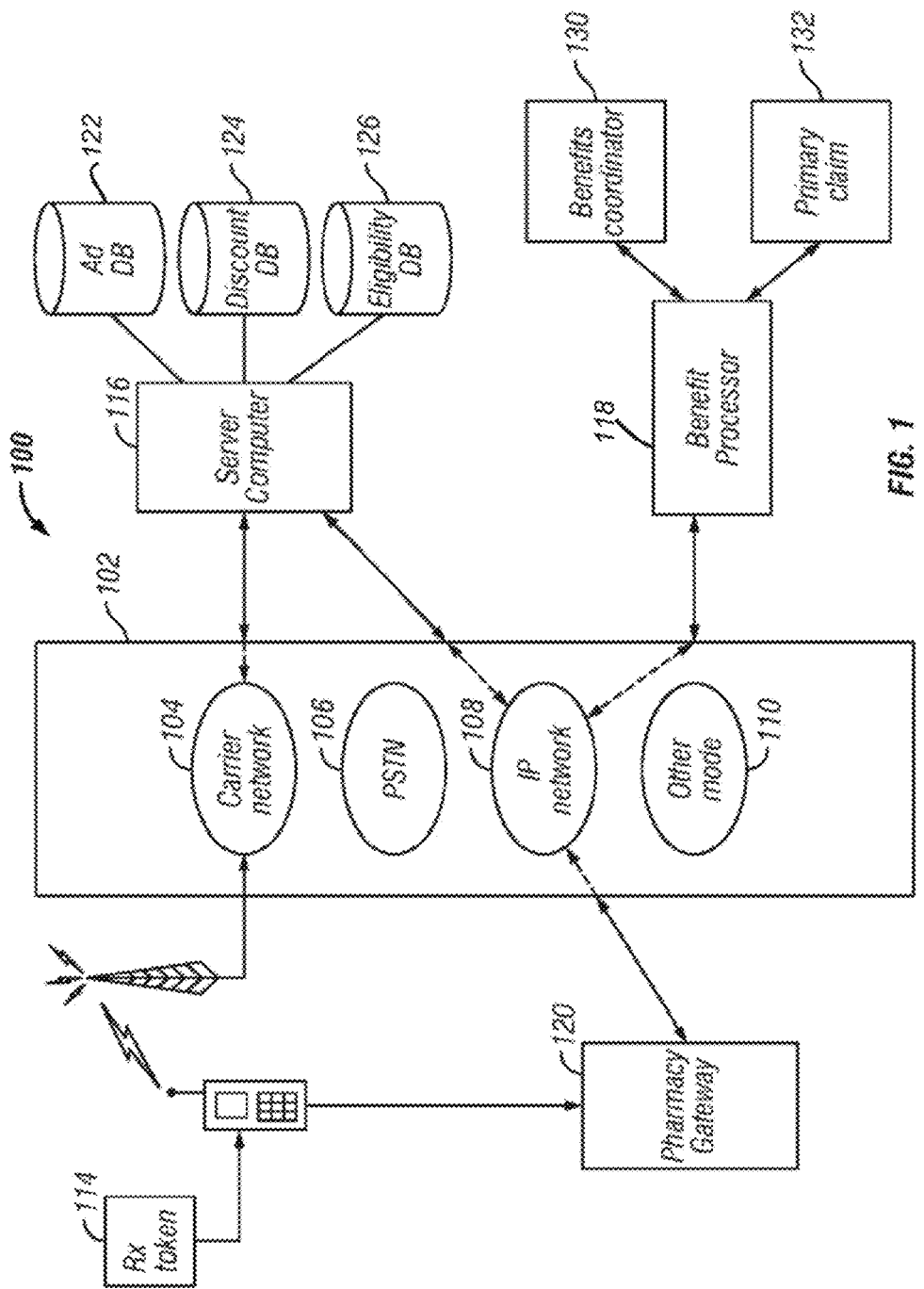
FIG. 1 illustrates a system for delivering a prescription drug discount to a cellular communications device over a cellular carrier network, according to certain embodiments of the invention.

Referring to FIG. 1, a system 100 for communicating with a prescription drug customer to provide drug discounts and aid drug therapy comprises one or more communications network 102. The network 102 includes a cellular carrier network (carrier network) 104, and can also include, for example, one or more of a public switched telephone network (PSTN) 106, a packet switched network (IP network) 108, and other channel or mode of communication 110. For convenience in discussion, the carrier network 104 is identified as such herein. Other communication networks, such as the PSTN 106, the IP network 108, and/or other channel or mode are sometimes individually or collectively referred to herein as "Other Networks." The term Other Networks, therefore, is intended to mean any one or more communications links which are not the carrier network 104. As will be understood, the carrier network 104, as well as the Other Networks, may be inter-linked or interconnected for communications between or among said networks or respective ones of them.

The system 100 also includes a cellular communications device 112. The cellular communications device 112 is communicatively connected to the carrier network 104. The cellular communications device 112 is any of a cellular radio transceiver capable of communicating messages, such as short message service (SMS), multimedia message service (MMS), enhanced message service (EMS), wireless access protocol service (WAP), and/or other message on the carrier network 104 to and from a destination serviced by the carrier network 104 and/or the Other Networks via communicative connection to the carrier network 104. Pluralities of the cellular communications device 112, as well as additional and varied types of cellular data, voice and information communicators, can concurrently communicatively connect to and communicate over the carrier network 104. For purposes of illustration in FIG. 1, the cellular communications device 112 is shown as a single unitized device; however, it is to be understood that the cellular communications device 112 may be any of a cellular telephone, cellular modem equipped laptop or personal digital assistant, similar cellular communicator, or a combination of any of these with other electronic device(s) and/or device components.

Figure 2:
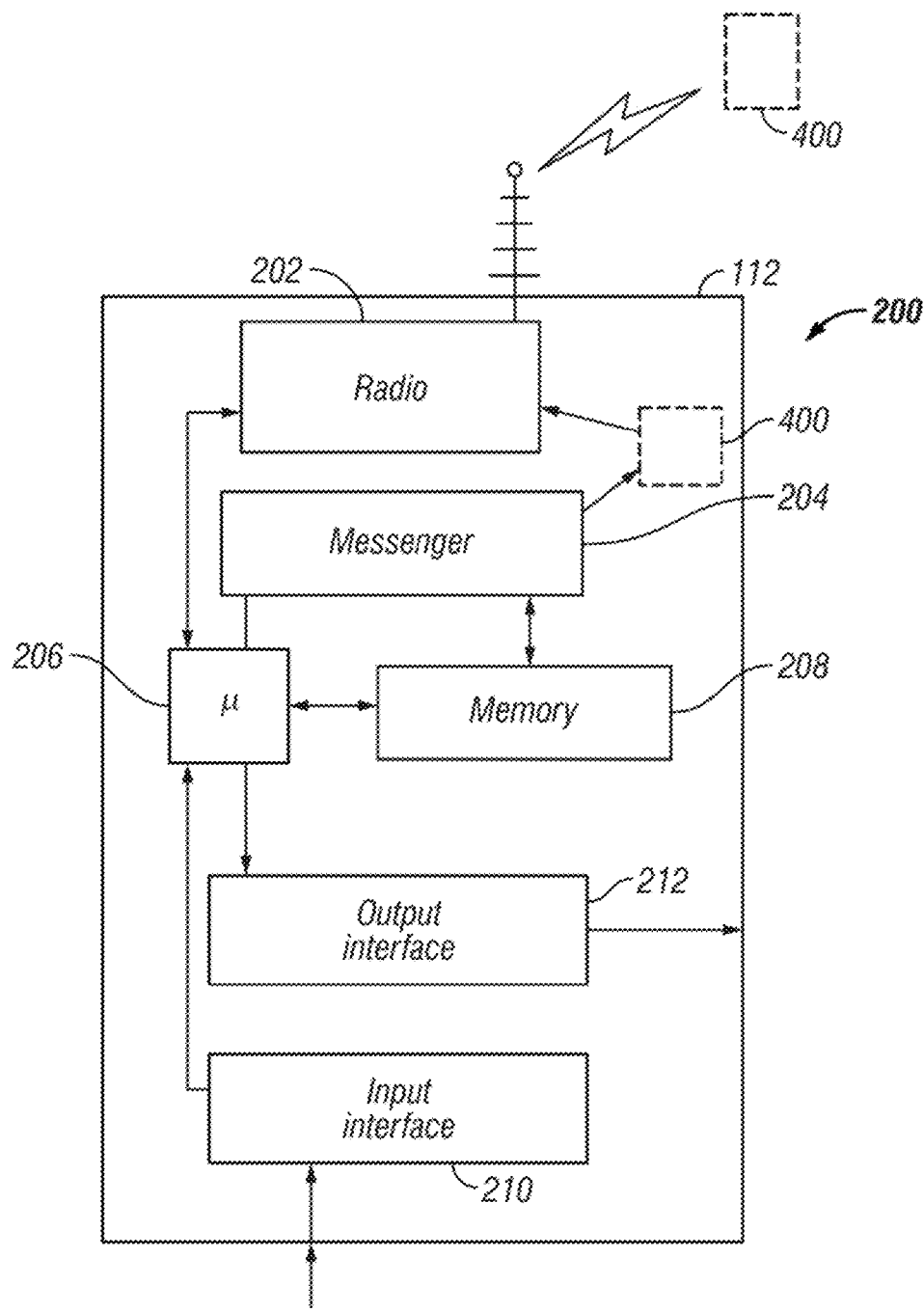
FIG. 2 illustrates an exemplary cellular communications device of the system of FIG. 1, according to certain embodiments of the invention.

Referring to FIG. 2, in conjunction with FIG. 1, the cellular communications device 112 of the system 100, for example, a cellular phone with messaging component(s), comprises a cellular radio 202, a messenger 204, a processor 206, a memory 208, an input interface 210 and an output interface 212. The processor 206 is connected to the messenger 204. The processor 206 is also connected to the memory 208, the input interface 210 and the output interface 212. The processor 206 can be a single microprocessor or other control circuit, or pluralities or combinations of these. The processor 206 controls the messenger 204, the memory 208, the input interface 210 and the output interface 210. The processor 206 can further be connected to the radio 202 for control of transmission and reception by the radio 202 on the carrier network 104. The messenger 204 is, for example, a microprocessor, logic circuit, messaging program stored in memory controlled by the processor 206, or pluralities or combinations, for initiating, creating, formatting, and transmitting, and receiving, constructing, transposing, and viewing, a cellular data message over the carrier network 104.

Figure 3:
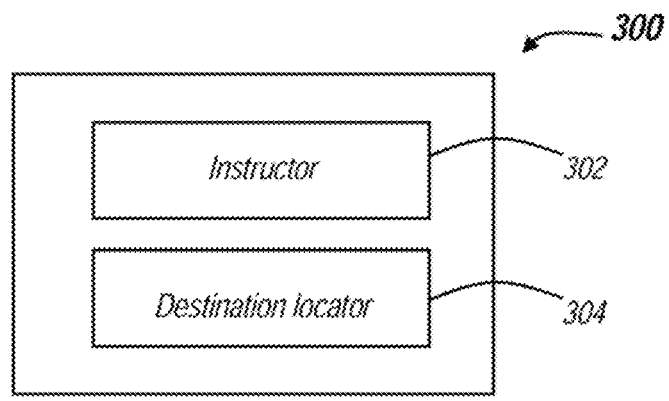
FIG. 3 illustrates a token structure of a prescription token of the system of FIG. 1, according to certain embodiments of the invention.

Referring to FIG. 3, in conjunction with FIGS. 1 and 2, the system 100 further comprises a prescription token (Rx token) 114 providing input to the cellular communications device 112. The Rx token 114 comprises a token structure 300, including at least one instructor 302 relative to the Rx token 114 and at least one destination locator 304 of the carrier network 104 (or of one of the Other Networks communicatively connected to the carrier network 104). The cellular communications device 112 processes the at least one instructor 302, such as upon input via the input interface 210, to generate the token structure 300 and store the token structure 300 in the memory 208. The at least one destination locator 304 targets the token structure 300 for communicative receipt by a server computer 116 (shown in FIG. 1) of the system 100. In addition to the at least one instructor 302 and the at least one destination locator 304, the token structure 400 can, but need not necessarily, comprise an authorization artifact, policy, or other article or component (not shown in detail in FIG. 3) of or for the Rx token 114.

The Rx token 114 is input to (or read or received by) the cellular communications device 112. For example, the Rx token 114, or representative features thereof, is entered to the input interface 210 of the cellular device 112, such as by a keypad, magnetic, infrared or radio frequency identification (RFID) reader, Bluetooth™ communicator or dongle, touch screen, or other interface component of the cellular communications device 112. Via the processor 206, in conjunction with the input interface 210 and the memory 208, as applicable, the token structure 300 of the Rx token 114 is saved in the memory 208. In certain embodiments, the Rx token 114 is a card, such as a plastic wallet card, representing the at least one instructor 302 and the destination address 304 provided to the user of the cellular device 112 for input by the user to the cellular device 112. Alternately, the Rx token 114 can be communicated to the cellular communications device 112 from an external source (not shown), via a communication interface (such as the radio 202 or another data input component) for message service, e-mail, website download, or via other component of the cellular communications device 112 capable of receiving such input. In other alternatives, the Rx token 114 can be pre-installed as an application or stored bits in programmed memory (e.g., ROM, EPROM, EEPROM) of the cellular communications device 112.

The Rx token 114 in certain embodiments is the token structure 300. As the token structure 300, the Rx token 114 is itself an input to, read into, and/or converted by the cellular communications device 112 to a communicative message artifact 400 transmitted by the cellular communications device 112 on the carrier network 104. Alternately, the token structure 300 is representative of the Rx token 114 but is not itself the Rx token 114. As an example, the Rx token 114 directs or activates an input to the cellular communication device 112 of the token structure 300, and the token structure 300 is thereby controlled by the Rx token 114. In such example, the Rx token 114 is not itself the token structure 300 input to the cellular communications device 112, and, in effect, is proxy for the token structure 300 as retained in the memory 208 of the cellular communication device 112.

According to certain examples, or in various alternatives, the Rx token 114 is or is included in the benefit element, or data representing the benefit element, passing through the switch 1104, 1304 or other devices of FIGS. 11-13, is orally or by text messaging provided by the phone or device when calling to provide the offer code 1418 or other relevant items of the offer code card 1402 of FIG. 14, or is provided by the enrollment form 1502 of FIG. 15 delivered to the server computer by a physician or provider communication device, or otherwise. In the case that the Rx token 114 is anything other than an input to or resident on the cellular communication device 112, the Rx token 114 may be provided to the server computer 116 other than through communications of the cellular communication device 112 with the server computer 116. For example, the benefit element is detected by a detector communicatively connected to the server computer 116 in such instance, the enrollment form is provided by a physician or provider communication device communicatively connected to the server computer in such instance, and so forth. In such instances, certain embodiments contemplate that opt-ins may be obtained from the cellular communications device 112 once the Rx token is received by the server computer 116.

Figure 4:
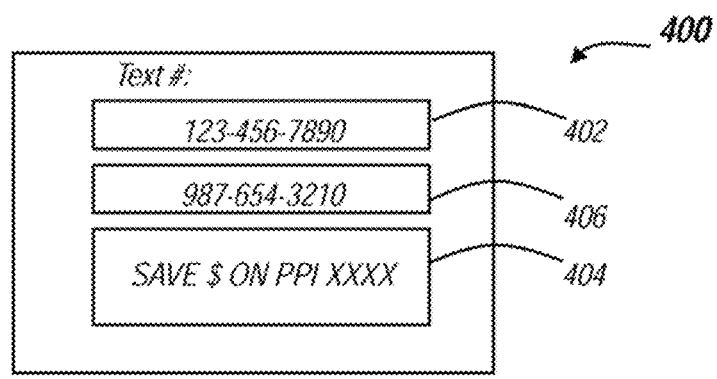
FIG. 4 illustrates a message artifact for the token structure of the system of FIG. 1, according to certain embodiments of the invention.

Referring to FIG. 4, in conjunction with FIGS. 1 and 2, the messenger 204, through operations of the processor 206 and the memory 208, processes and transforms the token structure 300 to create a message artifact 400 capable of communication by the cellular communications device 112 on the carrier network 104. The message artifact 400 comprises a destination address 402 of the network 102 for a receiver connected to the network 102, such as via the carrier network 104 or connected by the Other Networks to the carrier network 104. The message artifact 400 also comprises a request segment 404. The message artifact 400 can additionally comprise, for example, a privacy policy, restriction policy, other policy, and/or directive or control (collectively, the "policy 406), for authorizing the cellular communications device 112 to use the Rx token 114 and to communicate the message artifact 400 on the carrier network 104. In certain embodiments, the message artifact 400 is a cellular message, such as short message service (SMS), multimedia message service (MMS), enhanced message service (EMS), wireless access protocol service (WAP), and/or other message transmittable by the cellular communications device 112 over the carrier network 104 to the destination address 402 of the network 102.

The request segment 404 of the message artifact 400 designates a particular prescription drug, such as digital bits representing "PPIxxxx", where "PPI" is an identifying nomenclature for the class of the prescription drug and "xxxx" is an index number of the particular make/type of the drug. The destination address 402 controls routing of the message artifact 400 when transmitted on the carrier network 104 (and any applicable intermediate or destination pathways of the Other Networks connected to the carrier network 104) to the destination address 402 of the network 102. The policy 406, if included in the message artifact 400, accompanies and relates to the request segment 402 and the destination address 404 to maintain verification, authorization, and/or integrity of delivery of the message artifact 400 at the destination address 402 on transmission by the cellular communications device 112.

The message artifact 400, in certain examples, is or includes or evidences the opt-in(s) of the cellular communications device 112.

Figure 5:
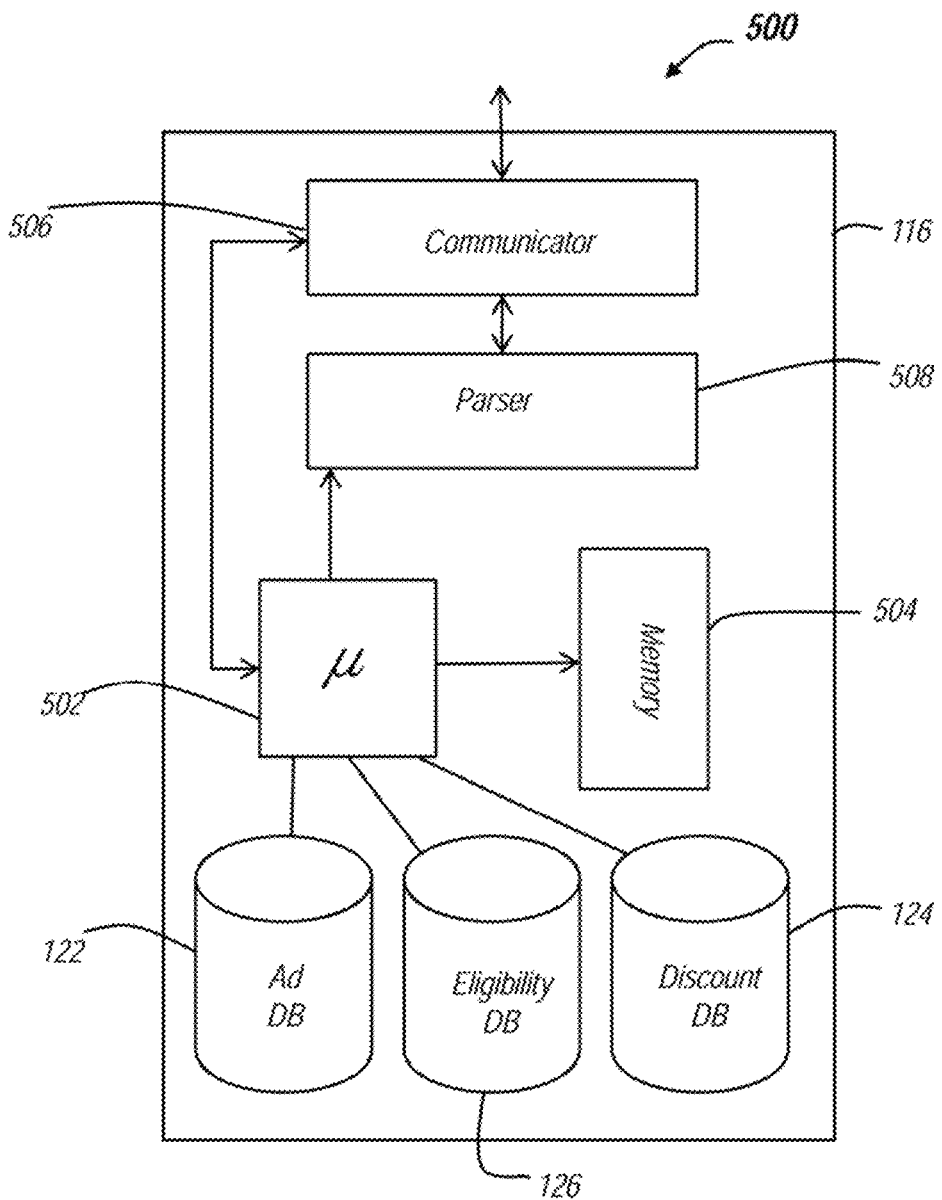
FIG. 5 illustrates an exemplary server computer of the system of FIG. 1, according to certain embodiments of the invention.

Referring to FIG. 5, in conjunction with FIG. 1, the server computer 116 of the system 100 is communicatively connected to the carrier network 104, directly or via one or more of the Other Networks communicatively connected to the carrier network 104. The server computer 116 has the destination address 404, such as by an IP address, cellular call number, or other communicative identifier of the server computer 116 on the network 102. The server computer 116 comprises a server processor 502, memory 504 connected to the server processor 502, at least one communicator device 506 connected to the server processor 502, and a message parser 508 connected to the at least one communicator device 506. The at least one communicator device 506 is a cellular modem, wired data connector (such as an Ethernet port), wireless data connector (such as a wireless area network (WLAN) modem), or other input/output component communicatively connected to the carrier network 104, directly or indirectly. The message parser 508 is a hardware component, software stored in memory, or combination, of the server computer 116 and can be or include the server processor 502.

The server computer 116 further comprises an ad processor 122, a discount processor 124 and an eligibility processor 126. Alternatively, the server computer 116 communicatively connects to at least certain of the ad processor 122, the discount processor 124 and/or the eligibility processor 126 external to the server computer 116. Each of the ad processor 122, the discount processor 124 and the eligibility processor 126 comprises or communicatively connects to a data processor, a memory, and a relational database stored in memory. In certain embodiments, the ad processor 122, the discount processor 124 and the eligibility processor 126 comprise at least certain of the processor 502, memory 504, and/or, if included in the server computer 116, one or more relational database (not shown in FIG. 5) stored in the memory 504.

Figure 6:
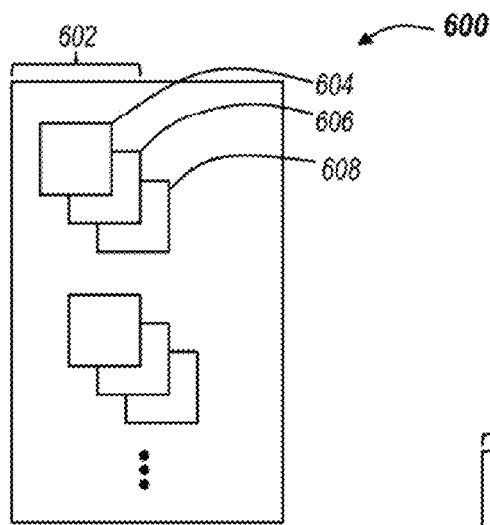
FIG. 6 illustrates an exemplary eligibility database of the server computer of the system of FIG. 1, according to certain embodiments of the invention.
Figure 7:
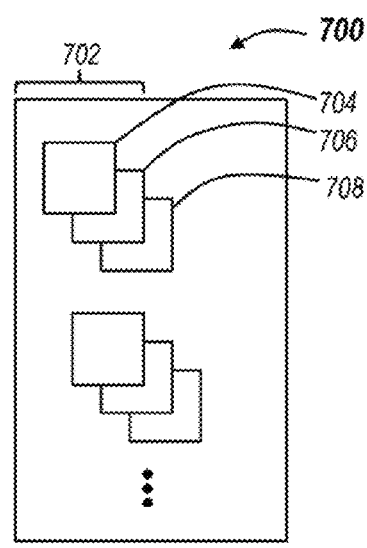
FIG. 7 illustrates an exemplary discount database of the server computer of the system of FIG. 1, according to certain embodiments of the invention.
Figure 8:
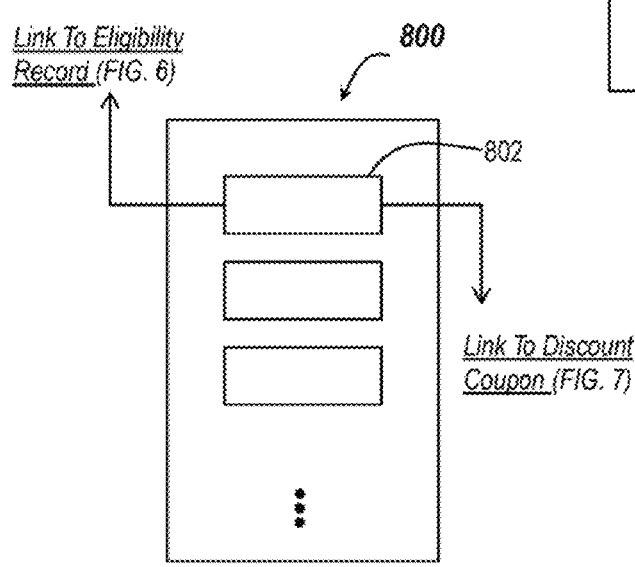
FIG. 8 illustrates an exemplary ad database of the server computer of the system of FIG. 1, according to certain embodiments of the invention.

Referring to FIGS. 6-8, in conjunction with FIGS. 1 and 5, the ad processor 122, the discount processor 124, and the eligibility processor 126, each comprise a processor, memory, and relational database stored in memory. Each database comprises at least one record and at least one field structure of each record. The database also comprises one or more logical relators for relationally associating each field structure with one or more records. Each field structure is (or points to) a respective data segment stored in memory. The data segment of each field structure can be any data, text, and/or logical operators, for example, a cellular phone identity (such as cell phone number), system opt-in permit, privacy policy, drug selector, transmit or receive message format, drug identifier, and other information bits. The database, operating via the processor and the memory, relationally organizes, and associates and selectively queries, sorts, filters, parses, retrieves, and reports, one or more of the data segments associated with applicable ones of the field structure. As will be appreciated, the ad database 122, the discount database 124 and the eligibility database 126 can comprise the same or different processor, memory and relational database stored in memory.

In exemplary embodiments, the respective relational database(s) of the eligibility processor 126 is illustrated in FIG. 6, of the discount database 124 is illustrated in FIG. 7, and of the ad database 122 is illustrated in FIG. 8. Referring to FIG. 6, the relational database 600 of the eligibility processor 126 comprises one or more eligibility records 602. Each of the eligibility records 602 comprises a cellular phone identity 604, a patient number 606, and an eligibility article 608. The phone identity 604 is relationally linked (i.e., associated) with the patient number 606, and the patient number 606 is relationally linked with the eligibility article 608.

Referring to FIG. 7, the relational database of the discount database 124 comprises one or more discount coupon 702. Each discount coupon 702 comprises a discount artifact 704, a pharmacy identity 706, and a drug unit 708. The pharmacy identity 706 is relationally linked to the drug unit 708. The discount artifact 704 is relationally linked to the drug unit 708 and, in certain embodiments, to the pharmacy identity 706. In certain embodiments, the discount artifact 704 is generated by the server processor 502 (of the server computer 116 of FIG. 1) via a program stored in memory (not shown in detail); for example, based on the drug unit 708, the pharmacy identity 706, and a particular one of the eligibility records 602, the discount program logically generates the discount artifact 704.

Referring to FIG. 8, the relational database of the ad database 122 comprises a plurality of ad messages 802. The ad messages 802 are relationally linked to the eligibility records 602 and the one or more discount coupon 702, either via processing by the server processor 502, via an ad program stored in memory (not shown in detail), by the eligibility processor 700 and discount processor 800, or combinations. Operations of the eligibility processor 126, the discount database 124, and the ad database 122 are later described in conjunction with operations of the server processor 502 and other aspects of the system 100.

Figure 9:
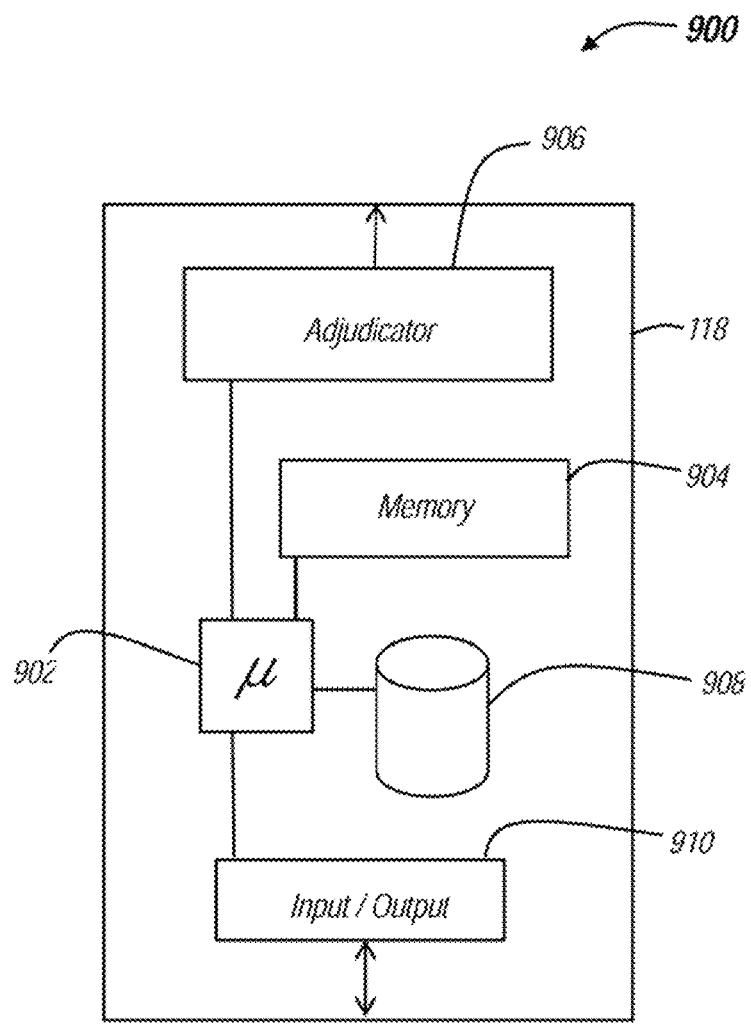
FIG. 9 illustrates an exemplary benefit processor of the system of FIG. 1, according to certain embodiments of the invention.

Referring to FIG. 9, in conjunction with FIG. 1, a benefit processor 118 comprises an input/output interface 910 communicatively connected, via one or more of the carrier network 104 and/or the Other Networks, to the server computer 116. In certain embodiments, the benefit processor 118 comprises a microprocessor 902, a benefit memory 904, an adjudicator 906, and a benefit database 908 stored in the benefit memory 1004. The microprocessor 902 connects to the input/output interface 910, the benefit database 908, the memory 904, and the adjudicator 906. The adjudicator 906 is, for example, a software program stored in memory or hardware logic component. In certain embodiments, the benefit processor 118 is a computer and the input/output interface 910 is a wired, wireless or cellular modem or other communicative element connected to the IP network 108 directly and/or, alternatively or in combination, indirectly via the network 102. In certain embodiments, the benefit processor 118 connects to the IP network 108 and communicates thereon with the server computer 116 via a web browser, file transfer protocol (ftp) or proprietary program stored in memory, proprietary protocol communicator, e-mail communicator, messaging system, electronic data interchange (EDI) system, or other device or connected component of the benefit processor 118.

The adjudicator 906 of the benefit processor 118 comprises, or is communicatively connected to, a benefits coordinator 130 and a primary claim negotiator 132. The benefits coordinator 130 and the primary claim negotiator 132 are each stores of insurance coverage data for patients obtaining prescription drugs via the system 100. An example of the benefit processor 118 is an insurance benefits processing company computer system or network and related database(s). In an exemplary embodiment, the benefits coordinator 130 administers Medicare prescription drug claims of patients and the primary claim negotiator 132 administers primary insurer prescription drug claims of patients.

Referring back to FIG. 1, a pharmacy gateway 120 communicatively connects, via network 102, to the benefit processor 118. The pharmacy gateway 120 is a computer, telephone, or other communicator device having one or more of a wired, wireless or cellular modem or analog voice transceiver communicative link to the benefit processor 118, for example, a local area network (LAN), a wireless area network (WLAN), enterprise sub-networks, router, switch, computer, the cellular network 104, the PSTN 106, the other channel or mode 110, switchboard, private branch exchange system, portions or sub-networks thereof, and other links. In certain embodiments, the pharmacy gateway 120 connects to the IP network 108 for communications with the benefit processor 118. The pharmacy gateway 120 in certain embodiments communicatively connects to the cellular communications device 112 via the carrier network 104. In alternate embodiments, the pharmacy gateway 120 communicates with the cellular communications device 112 by viewing a display of the cellular communications device 112, reading a file structure of the cellular device 112, communicating with the server computer 116 as proxy for the cellular communications device 112 (such as on the IP network 108 or the Other Networks), or via cellular or analog telephone call of the cellular communications device 112 or other device (not shown in detail).

In operation of the system 100, the token structure 300 of the Rx token 114 is captured to the memory 208 of the cellular communications device 112, such as via signal input to the input interface 210 of the cellular communications device 112 or as otherwise previously described. The processor 206 stores the token structure 300 in the memory 208. The messenger 204 is then initiated, and in conjunction with operations of the processor 206 and the memory 208, creates the message artifact 400 from the token structure 300. The messenger 204, in conjunction with the processor 206, controls the radio 202 to transmit the message artifact 400 to the destination address 402 for the server computer 116 over the carrier network 104.

In certain embodiments, upon capture of the token structure 300 of the Rx token 114 and further direction input to the input interface 210 of the cellular communications device 112, the messenger 204 is initiated by the processor 206 in response to signal of the input interface 210 (e.g., initiation of operations of the messenger 204 as an application program stored in memory via signal of the input interface 210). For example, a user of the cellular communications device 112 initiates the messenger 204 by instruction entry to the input interface 210. In other embodiments, the messenger 204 is initiated automatically on receipt or storage of the token structure 300 in the memory 208, or otherwise.

In certain alternatives, the Rx token 114 is or is included in the benefit element, or data representing the benefit element, passing through the switch 1104, 1304 or other devices of FIGS. 11-13, is orally or by text messaging provided by the phone or device when calling to provide the offer code 1418 or other relevant items of the offer code card 1402 of FIG. 14, or is provided by the enrollment form 1502 of FIG. 15 delivered to the server computer by a physician or provider communication device, or otherwise.

The messenger 204, under control of the processor 206, delivers the message artifact 400 to the radio 202 of the cellular communications device 112. The radio 202 transmits the message artifact 400 as a cellular message on the carrier network 104.

The server computer 116 receives the message artifact 400 sent by the cellular communications device 112 from the network 102 via the communicator 506. As received, the message artifact 400 is constructed and parsed by the server computer 116 for the token structure 300. The token structure 300, or portions, is saved in the server memory 504.

The server processor 502 of the server computer 116 performs a look-up in the eligibility database 126 for any of the eligibility records 602 containing (or otherwise relevant) to the token structure 300. For example, the server processor 502 filters the eligibility records 602 to determine if the at least one instructor 302, or portions, of the token structure 300 match any cellular phone identity 604 of the eligibility records 602. If match is not found, the server processor 502, in conjunction with the eligibility database 126 creates a new one of the eligibility records 602 for the cellular phone identity 604 and other details of the token structure 300 (i.e., in such instance, the created eligibility record is for a new patient/user with a cell phone not recognized as previously registered with the system). The server processor 502 then performs a look-up in the discount database 124 to retrieve the discount coupon 702 for the new eligibility record 602 created for the cellular phone identity 604. The discount coupon 702 comprises the discount artifact 704, the pharmacy identity 706 and the drug unit 708. For example, the discount coupon 702 obtained from the look-up provides information of a particular pharmacy and saving discount. The server computer 116 sends the discount coupon 702, as a message (e.g., SMS, MMS, EHS, WAP, or other message), to the cellular communications device 112 (either directly on the carrier network 104 or via the Other Networks communicatively connected to the carrier network 104). If, however, match is found in the look-up by the server computer 116 in the eligibility database 126 (e.g., the cellular phone identity 604 is present in at least one of the eligibility records, indicating a previously registered patient/user with a cell phone recognized as previously registered with the system), the applicable eligibility record(s) 602 for the at least one instructor 302 are retrieved by the server processor 502. The discount database 124 is then searched to determine the applicable discount coupon 702 relevant to the particular instructor 602 and eligibility record(s) 602. The server computer 116 then sends the discount coupon 702, as a message on the network 102, to the cellular communications device 112 for receipt from the carrier network 104.

After the applicable discount coupon 702 is sent as the message by the server computer 116, the messenger 204 of the cellular communications device 112 receives the discount coupon 702 over the carrier network 102. The processor 206 of the cellular communications device 112 processes and displays output via the output interface 212 representing the discount coupon 702. The discount coupon 702 is saved in the memory 208, either automatically on processing and display or by instruction to the input interface 210.

By direction to the input interface 210 by the user of the cellular communications device 112, the discount coupon 702 is presented to the pharmacy gateway 120. Delivery of the discount coupon 702 is, for example, via viewing of a display representing the discount coupon 702 on the cellular communications device 112 at the physical location of a pharmacy, communicative transmission of the discount coupon 702 by the cellular communications device 112 to the pharmacy gateway 120, such as over the carrier network 104, or communicative transmission of the discount coupon 702 to the pharmacy gateway 120 via one of the Other Networks, either by the cellular communications device 112 or another networked device.

On presentation of the discount coupon 702 to the pharmacy gateway 120, the pharmacy gateway 120 communicates to the benefit processor 118 the discount coupon 702, together with a prescription script corresponding to the discount coupon 702, applicable identifier for the drug of the prescription script (obtained by the patient from a physician), an identifier of the patient relevant to the prescription script, and other items (such as may be required by the benefit processor 118). The benefit processor 118 receives the communication, and processes a covered benefit related thereto. In processing the covered benefit, the adjudicator 906 of the benefit processor 118 accesses the benefits coordinator 130 and/or the primary claim negotiator 132. If the covered benefit is available from the benefits coordinator 130, then the benefit processor 118 communicates a coverage indicator to the pharmacy gateway 120. If the covered benefit is not available from the benefits coordinator 130, then the benefit processor 118 communicates a no coverage indicator to the pharmacy gateway 120.

If the pharmacy gateway 120 gateway receives a coverage indicator, then the pharmacy processes the prescription in typical manner, provides the patient a discount per the discount coupon 702, and charges the patient a price for the prescription reduced by the discount and the covered benefit. If the pharmacy gateway 120 receives a no coverage indicator, then the pharmacy processes the prescription in typical manner, provides the patient the discount per the discount coupon 702, and charges the patient a price for the prescription reduced by solely the discount.

Upon the benefit processor 118 communicating the coverage indicator or no coverage indicator to the pharmacy, the benefit processor 118 communicates to the server computer 116 an eligibility update notification. The eligibility update notification is received by the server computer 116, processed and stored in memory. The server processor 502 controls the eligibility processor 126 to change the eligibility records 602 for the patient number, for example, per a particular patient number 606 of the patient (as indicated by the eligibility update notification), corresponding to the particular prescription, such as by storing in memory a different eligibility status indicator in the relationally linked eligibility article 608 of the applicable eligibility record(s) 602.

These operations of the system 100 are repeated for each next Rx token 114 captured in and transmitted by the cellular communications device 112, with the result that each next Rx token 114 will result in change to the cellular communications device 112, the server computer 116, and the benefit processor 118 reflecting each prescription transaction by a patient associated with the particular cellular communications device 112.

Figure 10:
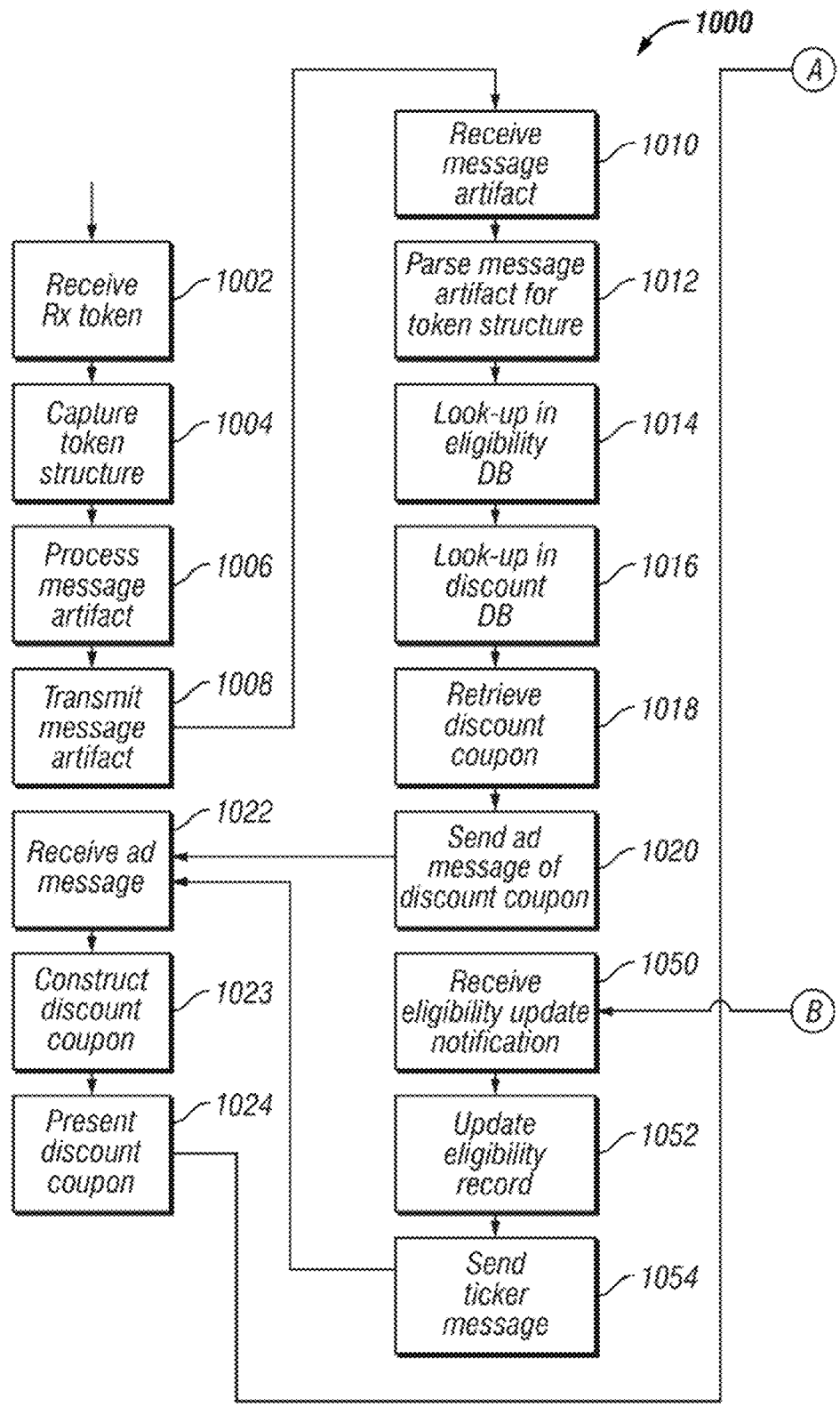
FIG. 10 illustrates a method of delivering a prescription drug discount to a cellular communications device over a cellular carrier network, according to certain embodiments of the invention.
Figure 10:
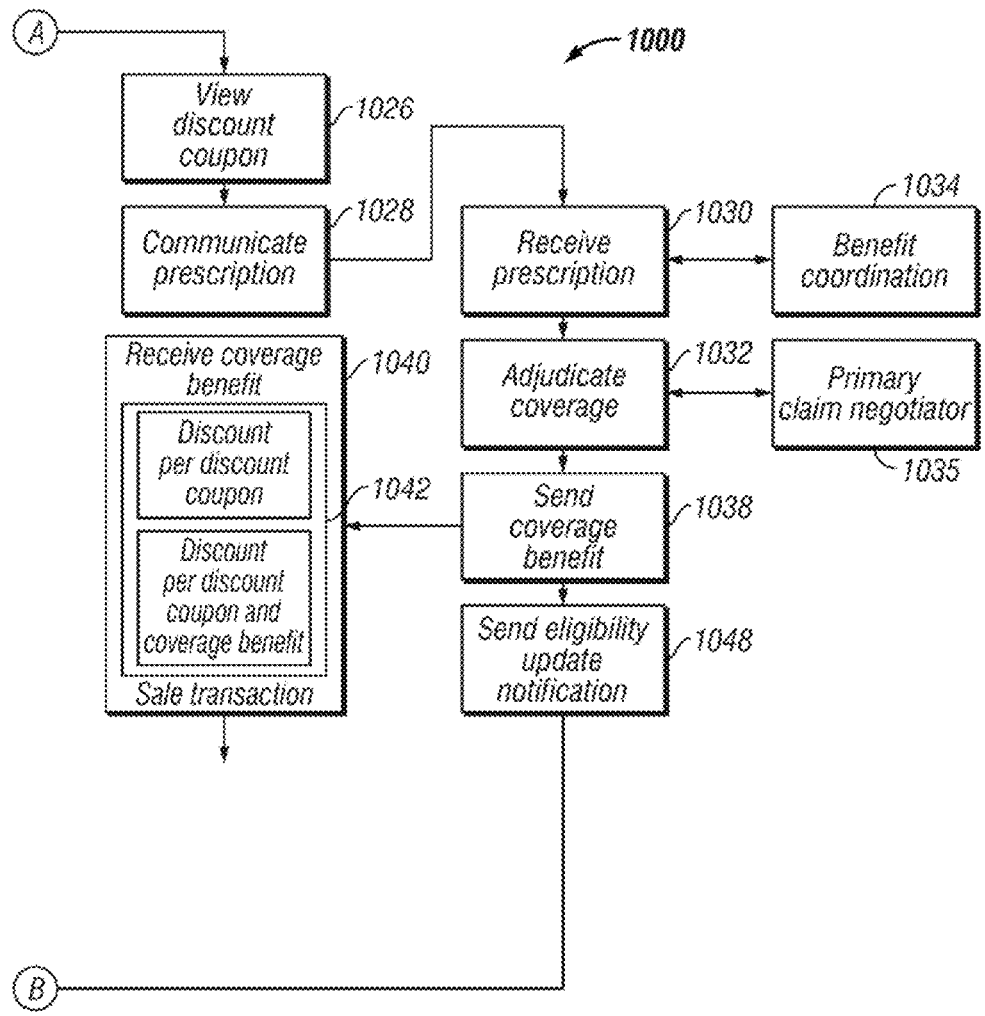

Referring to FIG. 10, a method 1000 of communicating with a prescription drug customer to provide drug discounts and aid drug therapy comprises a step 1002 of receiving the Rx token 114 by a user of a cellular communications device 112. For example, the Rx token 114 is obtained by a patient from a physician, together with a prescription script for a drug addressing the patient's malady. The token structure 300 of the Rx token 200 is input to the input interface 210 or otherwise captured in the memory 208 of the cellular communications device 112 in a step 1004. The cellular communications device 112 is, for example, a cell phone of the patient or care-provider of the patient.

In certain alternatives, the steps 1002 and 1004 are performed by the detector of FIGS. 11-13 by determining the benefit element, or data representing the benefit element, passing through the switch 1104, 1304 or other devices, and communicating with the server computer, by a beneficiary or communications device of the beneficiary by orally or by text messaging calling to provide the offer code 1418 or other relevant items of the offer code card 1402 of FIG. 14, or by a physician or provider communication device, or otherwise, by delivering the enrollment form 1502 of FIG. 15 to the server computer.

In a step 1006, the messenger 204 is initiated, such as by additional direction input to the input interface 210 or storage of the token structure 300 in memory 208, and the processor 206 of the cellular communications device 112 processes the token structure 300 to generate the message artifact 400 in respect of the token structure 300. The message artifact 400 is transmitted by the radio 202, under direction of the memory 208 and control of the processor 202, on the carrier network 104. The message artifact 400 is, for example, a cellular message transmitted by the cellular communications device 112, such as an SMS, MMS, EMS, WAP, or other message, directed to the destination address 402 of the network 102 for the server computer 116.

In a step 1010, the server computer 116 receives the message artifact 400 as communicated to the server computer 116 by the network 102. The network 102 can be the carrier network 104, or another of the Other Networks communicatively connected to the carrier network 104. On receipt of the message artifact 400 by the server computer 116, the message parser 508 of the server computer 116 constructs, parses and translates the message artifact 400 to recover the token structure 300 in a step 1012.

The server computer 116 performs a logical look-up in a step 1014 of an aspect of the token structure 300 in the eligibility database 126. In the step 1014, the eligibility records 602 are filtered to determine any match to the at least one instructor 302, or portions, of the token structure 300. For example, the at least one instructor 302 of the token structure 300 includes the cellular phone identity 604, such as cell phone number for the cellular communications device 112 and a designation for particular prescription drug of the prescription script provided by the physician to the patient-user of the cellular communications device 112. In certain embodiments, the at least one instructor 302 includes a message, such as "Save $ on PPIxxxx" where PPIxxxx identifies the class and particular make/type of drug of the prescription script.

The server computer 116 performs a next logical look-up in a step 1016 of the discount coupon 702 applicable to the prescription drug (such as PPIxxxx) and particular eligibility records 602, if any, located in the step 1014. If none of the eligibility records 602 are located in the step 1014, the server computer 116, in a step 1018, retrieves the ad message(s) 802 for the particular discount coupon 702 of the step 1014. If eligibility records are located in the step 1014, the server computer 116 in the step 1018, instead, retrieves a different one or more of the ad message 802 for the discount coupon 702 of the step 1014. In a step 1020, the server computer 116 sends the ad message 802 retrieved in the step 1018, for receipt by the cellular communications device 112 over the carrier network 104. For example, in the step 1020, the server computer 116 sends the ad message 802 on the network 102, such as by an SMS, MMS, EMS, WAP or other message, to the phone number for the cellular communications device 112.

The cellular communications device 112 receives the ad message 802 in a step 1022. In a step 1023, the ad message 802 is constructed, parsed, saved and displayed by the cellular communications device 112 in the form of the discount coupon 702. In a step 1024, the user of the cellular communications device 112 presents the discount coupon 702, together with the prescription script, to a pharmacy. The presenting step 1024 comprises, for example, display of the discount coupon 702 on the cellular communications device 112 at the physical location of the pharmacy (e.g., the cellular communications device 112 is carried to the pharmacy and the discount coupon 702 is shown to a pharmacist via the output interface 212), transfer of the discount coupon 702 to the pharmacy gateway 120 for receipt by the pharmacy (e.g., the cellular communications device 112 communicates the discount coupon 702 to the pharmacy gateway 120 by cellular message, website upload, ftp transfer, or other), or other mode (e.g., the discount coupon 702 is delivered to the pharmacy gateway by another network device, such as a networked computer, capable of communicating on the network 100, the discount coupon 702 is printed from the cellular communications device 112 and the print copy is given to the pharmacy, or otherwise).

On presentation of the discount coupon 702 in the step 1024, the pharmacy gateway 120 (or pharmacy, as applicable) views the discount coupon 702 in a step 1026. The pharmacy gateway 120, in a step 1028, communicates the prescription script to the benefit processor 118, together with identification of the applicable patient and any additional information required by the benefit processor 118. For example, the pharmacy gateway 120 communicates in the step 1028 via the network 102, with the benefit processor 118.

In a step 1030, the benefit processor 118 receives the prescription script, together with the additional information. The benefit processor 118 adjudicates the coverage benefit applicable to the prescription script and patient in a step 1032. The step of adjudicating 1032 the coverage benefit includes either: a step of communicating 1034 with the benefits coordinator 130 if the benefits coordinator 130 provides the coverage benefit, a step of communicating 1036 with the primary claim negotiator 132 if the benefits coordinator 130 does not provide the coverage benefit, or combination. In response to the step of adjudicating 1032, the benefit processor 118, in a step 1038, determines the coverage indicator/no coverage indicator, in respect of the coverage benefit from the step of adjudicating 1032, and communicates the coverage indicator or otherwise, the no coverage indicator, to the pharmacy gateway 120 (or pharmacy, depending on mode of communication).

In a step 1040, the pharmacy gateway 120 (or pharmacy, as applicable) receives the coverage indicator or no coverage indicator, as applies. If the pharmacy gateway 120 receives the coverage indicator, the pharmacy gateway 120 (or pharmacy) in a step 1042 provides the patient a discount in price, per the discount coupon 702, and less the coverage benefit per the coverage indicator, in a sale transaction of the prescription drug according to the prescription script. If, on the other hand, the pharmacy gateway 120 receives the no coverage indicator, the pharmacy gateway 120 (or pharmacy) in the step 1042 provides the patient a discount in price, per the discount coupon 702 (without any coverage benefit reduction), in a sale transaction of the prescription drug according to the prescription script.

On completion of the step 1038 by the benefit processor 118, the benefit processor 118 communicates the eligibility update notification to the server computer 118 in a step 1048. The server computer 118 receives the eligibility update notification in a step 1050. Communication of the eligibility update notification is via the network 102. Upon the receiving step 1050, the eligibility update notification is read by the server computer 118. In a step 1052, the server processor 502, in response to the eligibility update notification, controls the eligibility processor 126 to change the eligibility records 602 stored in memory, for the patient number 606 corresponding to the eligibility update notification and prescription. For example, an eligibility status indicator in the related eligibility article 608 of the eligibility records 602 is modified to evidence that the sale transaction was completed for the prescription drug, with the applicable discount in price (i.e., either per discount coupon and coverage benefit reduction, if covered benefit; or per discount coupon, if no covered benefit).

The server computer, thereafter, in a step 1054, based on the eligibility records 602 as then existing for each respective patient number 606 and eligibility article 608, can send ticker reminder messages to the cellular communications device 112. In the step 1048, for example, the eligibility records 602 are periodically (e.g., daily) filtered and processed under control of the eligibility processor 126, to detect date(s) when refills of the prescription drug (and/or related or other products or services) would be needed by the relevant patient. In the step 1054, a ticker reminder message is sent to the cellular communications device 112 associated with the relevant patient per the cellular phone identity 604 of the eligibility records 602. The ticker reminder message is an SMS, MMS, EMS, WAP or other cellular message, sent by the server computer 116 on the network 102 directed to the carrier network 104, for receipt from the carrier network 104 by the cellular communications device 112 of the relevant patient.

Various alternatives and additions are possible in the foregoing embodiments. In certain alternatives, the discount per the discount coupon 702 may be provided by other than the pharmacy, such as by an insurer (e.g., to encourage patient participation and compliance to drug therapy regimen), a physician (e.g., to advertise), a pharmacy-related entity (e.g., to advertise products or services available at the pharmacy in addition to the prescription drug), and others. The discount coupon 702 can relate to a discount associated with any device or entity of the system or any other or external source. The server computer 116 or related discount database 126, alternatively, can be managed or provided by an external device or network to the system 100, such as by an input to the system 100. In certain alternatives, the benefit processor 118 and pharmacy gateway 120 are not included in the system 100, and/or the server computer 116 provides the functionalities of the benefit processor 118 and the pharmacy gateway 120. An example of such scenario is a pharmacy conglomerate or pharmacy/insurer combination which provides the functionalities of the server computer 116, benefit processor 118 and pharmacy gateway 120 either directly without the network 102 or via other modes and devices.

In other alternatives, modifications and additions, the system 100 permits advertising, via the pharmacy gateway 120, the server computer 116, and/or benefit processor 118, based on the eligibility records 602 or other elements of the system 100. For example, the eligibility records 602 can provide information and data of distinct patients (or communication devices of or related to those patients). Accumulation of such information and data in the manner of targeted cellular message communications from the patient to a particular destination of the network, and security protected channels of communications between pharmacy and benefit providers, affords security of communications of patient information and, yet, allows for targeted advertising delivery to the patient by such secure channels. Through communicative connection to the eligibility records 602, any authorized device can direct or control the discount database 124, such as to make available particular form of the discount coupon 702 (and thus the discount, for example, if pricing changes, new discount items are advertised, etc.). Similarly, the server computer 116 can be controlled through such communicative connection, such as to send cellular messages to the cellular communications device 112 alerting to additional items, with directed timing or other criteria.

An example implementation of the foregoing embodiments follows:

A physician writes a prescription script and provides the patient with the script and a Rx token. The Rx token includes, for example, a HIPAA/privacy disclaimer and directions for input to a cellular phone of the patient. The patient inputs a token structure to the cell phone and commences a messenger of the cell phone to create a text message according to the directions of the Rx token and representing the token structure. The text message is an SMS message for transmission by the cellular phone on the cellular carrier network servicing the phone. The text message, per the directions, includes the text "Save $ on PPIxxxx" and is transmitted to a phone number xxx-xxx-xxxx per the directions.

The text message is received over a network, either the cellular carrier network or another network connected to the cellular carrier network, at the phone number (or at a designated location of the network, such as IP address, at which the message is proxied to the phone number). The text message is interpreted by a savings manager center, such as a server computer. The savings manager center searches database(s) records relevant to the received message, and responds to the cell phone via the cell phone number, with a response text message. This response text message includes a direction for a particular pharmacy, pharmacy instructions, and patient reference, such as "To save $ now, have [Pharmacy ABC] submit prescription drug claim to BIN XXXXXX & Group#PPI25 with ID#YM12345. Usage constitutes opt-in for follow-up" (e.g., 132 characters). This response text message is delivered by the cellular carrier network to the cell phone (or, in certain scenarios, the message is maintained by a message center accessible to the cell phone).

The cell phone receives the text message from the savings manager center. The patient (or care-giver, etc.) then presents the pharmacy (i.e., Pharmacy ABC) with the text message received on the cell phone, together with the prescription script obtained from the physician. The pharmacy views the text message, such as via the cell phone display, and the pharmacy submits the prescription to a benefit processor (such as a Coordinator of Benefits, primary insurer, or other) for adjudication of benefit coverage applicable to the patient and prescription of the prescription script. The benefit processor adjudicates the prescription benefit coverage with a benefits coordinator of Medicare, if applicable, and/or a primary insurer, as may apply. If the prescription is covered by Medicare, the benefit processor processes the claim to buy down the patient's co-pay to $XX with a maximum benefit of $XX. If the prescription is not covered or only partially covered by Medicare, the benefit processor processes the claim under primary insurance coverage for a cash paying patient (or as rejected under Medicare as Drug Not Covered (70) or Prior Authorization Required (75)).

On adjudication by the benefit processor, the benefit processor communicates the applicable benefit coverage to the pharmacy. The benefit processor additionally sends details of the prescription benefit coverage and adjudication to the savings manager center. The details communicated to the savings manager center contain NCPDP (National Council for Prescription Drug Program) fields, as follows: Patient or Cardholder First Name, Patient or Cardholder Last Name, Patient or Cardholder Date of Birth, Patient or Cardholder Gender, Prescriber ID, Insurer ID, Primary CoPay, Pharmacy ID, COB (Coordination of Benefits, i.e., Medicare) indicator/value, NDC (National Drug Code) #, Quantity Dispensed, and Days Supply.

The savings manager center, based on these received details, creates and sends a follow-up text message to the cellular phone of the patient. If prescription benefit coverage has been successfully adjudicated through the benefits coordinator of Medicare, the follow-up text message includes a compliance message on 50% utilization of maximum benefit, such as "For additional Rx savings, please visit website www.textRxSavings.com to complete a survey about PPIxxxx." If, on the other hand, the prescription is not covered by Medicare, the follow-up text message includes direction to send a prior authorization inquiry immediately, such as "No plan coverage for PPIxxxx. If insurance denied PPIxxxx, we want to help. Text plan name to request coverage or none if no Rx plan" (e.g., 132 characters). On receiving the follow-up text message on the cellular phone of the patient, the patient views the message and takes subsequent action. For example, as directed by the follow-up message, the patient can visit the listed website or send a text message to the savings manager center.

The savings manager center additionally, based on the details received from the benefit processor, updates eligibility records for the particular patient, prescription, cellular phone identity/number and any other applicable modifications. The savings manager center communicates the update by the savings manager center to the benefit processor to provide additional benefit coverage discount. In response to the communication, the benefit processor updates a benefit database to register that a benefit is extended for a certain number of refills of the prescription, for a specific time period, and/or for a specified total dollar benefit. The update to the benefit database is thereafter reflected for the adjudication of any next prescription drug coverage in connection with refill, new prescription, or as otherwise applicable for the particular patient.

In the foregoing specification, the invention has been described with reference to specific embodiments. However, one of ordinary skill in the art appreciates that various modifications and changes can be made without departing from the scope of the present invention as set forth in the claims below.

Accordingly, the specification and figures are to be regarded in an illustrative rather than a restrictive sense, and all such modifications are intended to be included within the scope of the present invention.

Benefits, other advantages, and solutions to problems have been described above with regard to specific embodiments. However, the benefits, advantages, solutions to problems and device(s), connection(s) and element(s) that may cause any benefit, advantage, or solution to occur or become more pronounced are not to be construed as a critical, required, or essential feature or element of any or all the claims. As used herein, the terms "comprises, "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A system for requesting and collecting an opt-in from an entity via a communications device of the entity communicatively connected to a communications network, the communications device having a unique identifier address of the communications network, comprising:
   a server computer communicatively connected to the communications network;
   a data channel for communicating the unique identifier address;
   a detector communicatively connected to the data channel to determine the unique identifier address communicated on the data channel;
   a dispatcher communicatively connected to and controlled by the server computer;
   an opt-in request message created by the dispatcher and directed to the communications device at the unique identifier address of the communications network;
   a database communicatively connected to and controlled by the server computer; and
   a record of the database created by the database for the communications device of the unique identifier address, the record includes items representing the opt-in request message and unique identifier address;
   wherein the server computer communicates the opt-in request message to the communications device over the communications network.

2. The system of claim 1, further comprising:
   a reply message of the opt-in received by the server computer over the communications network from the communications device having the unique identifier address;
   wherein the server computer controls the database to update the record for the communications device to reflect the received reply message of the opt-in from the communications device.

3. The system of claim 2, wherein the opt-in request message seeks HIPAA authorization of the communications device and the reply message of the opt-in is the HIPAA authorization of the communications device and the entity.

4. The system of claim 1, wherein the data channel is a switch of a prescription drug benefit system.

5. The system of claim 1, wherein the data channel is an exchange device of a prescription drug benefit system.

6. A method for requesting and collecting an opt-in from an entity via a communications device of the entity communicatively connected to a communications network, the communications device having a unique identifier address of the communications network, comprising the steps of:

detecting the unique identifier address passing through a data channel communicating the unique identifier address;

receiving the unique identifier address from the step of detecting by a server computer;

creating an opt-in request message directed to the unique identifier address;

communicating the opt-in request message over the communications network to the unique identifier address for receipt by the communications device; and creating a record of a database representing the opt-in request message and the unique identifier address.

7. The method of claim 6, further comprising the steps of:

receiving a reply message of the opt-in from the communications device over the communications network by the server computer;

updating the record of the database for the communications device and the opt-in request message, to reflect receipt of the reply message of the opt-in from the step of receiving.

8. The method of claim 7, wherein the opt-in request message seeks HIPAA authorization of the communications device and the reply message of the opt-in is the HIPAA authorization of the communications device and the entity.

9. The method of claim 6, wherein the data channel is a switch of a prescription drug benefit system.

10. The system of claim 6, wherein the data channel is an exchange device of a prescription drug benefit system.

11. A system for requesting and collecting an opt-in from an entity via a communications device of the entity communicatively connected to a communications network, the communications device having a unique identifier address of the communications network, comprising:

a server computer communicatively connected to the communications network;

an enrollment form communicatively connected to the server computer, the enrollment form includes the unique identifier address;

a dispatcher communicatively connected to and controlled by the server computer;

an opt-in request message created by the dispatcher and directed to the communications device at the unique identifier address of the communications network;

a database communicatively connected to and controlled by the server computer; and a record of the database created by the database for the communications device of the unique identifier address, the record includes items representing the opt-in request message and unique identifier address;

wherein the server computer communicates the opt-in request message to the communications device over the communications network.

12. The system of claim 11, further comprising:

a reply message of the opt-in received by the server computer over the communications network from the communications device having the unique identifier address;

wherein the server computer controls the database to update the record for the communications device to reflect the received reply message of the opt-in from the communications device.

13. The system of claim 12, wherein the opt-in request message seeks HIPAA authorization of the communications device and the reply message of the opt-in is the HIPAA authorization of the communications device and the entity.

14. The system of claim 11, further comprising:

a provider device communicatively connected to the server computer, capable of input to create the enrollment form;

wherein the enrollment form is communicated to the server computer by the provider device.

15. The system of claim 14, further comprising:

an interactive form served by the server computer to the provider device, the provider device, via input to the interactive form by the provider device, creates the enrollment form for communication to the server computer.

16. The system of claim 11, wherein the enrollment form relates to a prescription drug benefit.

17. A method for requesting and collecting an opt-in from an entity via a communications device of the entity communicatively connected to a communications network, the communications device having a unique identifier address of the communications network, comprising the steps of:

receiving an enrollment form that includes the unique identifier address, by a server computer communicatively connected to the communications network;

creating an opt-in request message based on the enrollment form, directed to the unique identifier address;

communicating the opt-in request message over the communications network to the unique identifier address for receipt by the communications device; and creating a record of a database representing the opt-in request message and the unique identifier address.

18. The method of claim 17, further comprising the steps of:

receiving a reply message of the opt-in from the communications device over the communications network by the server computer;

updating the record of the database for the communications device and the opt-in request message, to reflect receipt of the reply message of the opt-in from the step of receiving.

19. The method of claim 18, wherein the opt-in request message seeks HIPAA authorization of the communications device and the reply message of the opt-in is the HIPAA authorization of the communications device and the entity.

20. The method of claim 17, further comprising the steps of:

delivering an interactive form by the server computer, to a provider device for input to create the enrollment form; and receiving by the server computer the enrollment form from the provider device.

21. The method of claim 20, further comprising:

delivering by the server computer the interactive form, capable of input to create the enrollment form, to the provider device for input.

22. The method of claim 17, wherein the enrollment form relates to a prescription drug benefit.

23. A system for requesting and collecting an opt-in from an entity via a communications device of the entity communicatively connected to a communications network, the communications device having a unique identifier address of the communications network, comprising:

a server computer communicatively connected to the communications network;

an offer card including at least a call number and an offer code, the offer code and the unique identifier address received by the server computer via the call number over the communications network from the communications device;

a dispatcher communicatively connected to and controlled by the server computer;

an opt-in request message created by the dispatcher to correspond to the offer code, and directed to the communications device at the unique identifier address of the communications network;

a database communicatively connected to and controlled by the server computer; and a record of the database created by the database for the communications device of the unique identifier address, the record includes items representing the opt-in request message and unique identifier address;

wherein the server computer communicates the opt-in request message to the communications device over the communications network.

24. The system of claim 23, further comprising:

a reply message of the opt-in received by the server computer over the communications network from the communications device having the unique identifier address;

wherein the server computer controls the database to update the record for the communications device to reflect the received reply message of the opt-in from the communications device.

25. The system of claim 24, wherein the opt-in request message seeks HIPAA authorization of the communications device and the reply message of the opt-in is the HIPAA authorization of the communications device and the entity.

26. The system of claim 23, wherein the communications network includes at least a cellular text messaging link.

27. The system of claim 23, wherein the communications network includes at least a multimedia messaging service (MMS) messaging link.

28. The system of claim 11, wherein the offer card relates to a prescription drug benefit.

29. A method of requesting and collecting an opt-in for HIPAA authorization from an entity via a communications device of the entity communicatively connected to a communications network, the communications device having a unique identifier address of the communications network, the communications network includes a text messaging link to the communications device, comprising:

receiving by a server computer communicatively connected to the communications network, the unique identifier address of the communications device;

creating an opt-in request message directed to the unique identifier address;

communicating the opt-in request message over the communications network by the server computer to the unique identifier address, for receipt by the communications device over the text messaging link; and creating a record of a database representing the opt-in request message and the unique identifier address.

30. The method of claim 29, further comprising the steps of:

receiving a reply message of the opt-in from the communications network by the server computer, the reply message of the opt-in sent by the communications device over the text messaging link;

updating the record of the database for the communications device and the opt-in request message, to reflect receipt of the reply message of the opt-in from the step of receiving.

31. The method of claim 30, wherein the opt-in request message seeks HIPAA authorization of the communications device and the reply message of the opt-in is the HIPAA authorization of the communications device and the entity.

32. The method of claim 29, wherein the step of communicating includes a multimedia messaging service (MMS) message as the opt-in request message.

33. The method of claim 31, wherein the step of receiving the reply message includes a simple messaging service (SMS) message as the reply message of the opt-in.

34. The method of claim 29, wherein the step of receiving regards a prescription drug benefit.

35. The method of claim 31, wherein the step of receiving regards a prescription drug benefit.

* * * * *